US008609643B2

(12) United States Patent
DeLuca et al.

(10) Patent No.: US 8,609,643 B2
(45) Date of Patent: Dec. 17, 2013

(54) 2-METHYLENE-(20S,25R)-19,26-DINOR-VITAMIN D ANALOGS

(75) Inventors: Hector F. DeLuca, Deerfield, WI (US); Margaret Clagett-Dame, Deerfield, WI (US); Lori A. Plum, Arena, WI (US); Grazia Chiellini, Madison, WI (US); Pawel Grzywacz, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 418 days.

(21) Appl. No.: 12/343,586

(22) Filed: Dec. 24, 2008

(65) Prior Publication Data

US 2009/0170820 A1 Jul. 2, 2009

Related U.S. Application Data

(60) Provisional application No. 61/017,226, filed on Dec. 28, 2007.

(51) Int. Cl.
*A61K 31/593* (2006.01)
*C07C 401/00* (2006.01)
*A61P 17/06* (2006.01)
*A61P 1/00* (2006.01)
*A61P 17/00* (2006.01)
*A61P 37/00* (2006.01)

(52) U.S. Cl.
USPC .......................................... 514/167; 552/653

(58) Field of Classification Search
USPC .......................................... 514/167; 552/653
See application file for complete search history.

(56) References Cited

U.S. PATENT DOCUMENTS

| | | | |
|---|---|---|---|
| 4,666,634 | A | 5/1987 | Miyamoto et al. |
| 5,086,191 | A | 2/1992 | DeLuca et al. |
| 5,536,713 | A | 7/1996 | DeLuca et al. |
| 5,843,928 | A | 12/1998 | DeLuca et al. |
| 5,936,133 | A | 8/1999 | DeLuca et al. |
| 5,945,410 | A | 8/1999 | DeLuca et al. |
| 6,566,352 | B1 | 5/2003 | DeLuca et al. |
| 6,579,861 | B2 | 6/2003 | DeLuca et al. |
| 6,627,622 | B2 | 9/2003 | DeLuca et al. |
| 7,241,909 | B2 * | 7/2007 | DeLuca et al. ............... 552/653 |

OTHER PUBLICATIONS

Arbour et al., "A Highly Sensitive Method for Large-Scale Measurements of 1,25-Dihydroxyvitamin D," Analytical Biochemistry, vol. 255, pp. 148-154, (1998).
Baggiolini et al., "Stereocontrolled Total Synthesis of 1α,25-Dihydroxycholecalciferol and 1α,25-Dihydroxyergocalciferol," Journal of Organic Chemistry, 51, pp. 3098-3108, (1986).
Collins et al, "Normal Functional Characteristics of Cultured Human Promyelocytic Leukemia Cells (HL-60) After Inducation of Differentiation by Dimethylsulfoxide," The Journal of Experimental Medicine, vol. 149, pp. 969-974, (1979).
Darwish et al, "Identification of Transcription Factor That Binds to the Promoter Region of the Human Parathyroid Hormone Gene," Archives of Biochemistry and Biophysics, vol. 365, No. 1, pp. 123-130, (1999).
Fall et al, "Vitamin D Heterocyclic Analogues. Part 1: A Stereoselective Route to CD Systems with Pyrazole Rings in their Side Chains," Tetrahedron Letters 43, pp. 1433-1436, (2002).
Lythgoe et al, "Calciferol and its Relatives. Part22. A Direct Total Synthesis of Vitamin D2 and Vitamin D3," J. Chem. Soc. Perkin Trans. 1, p. 590, (1978).
Lythgoe, "Synthetic Approaches to Vitamin D and its Relatives," Chem. Soc. Rev. 9, p. 449, (1983).
Miyamoto et al, "Synthetic Studies of Vitamin D Analogues. XIV. Synthesis and Calcium Regulating Activity of Vitamin D3 Analogues Bearing a Hydroxyalkoxy Group at the 2β-Position," Chem. Pharm. Bull., vol. 41 No. 6, pp. 1111-1113, (1993).
Nishii et al, "The Development of Vitamin D3 Analogues for the Treatment of Osteoporosis," Osteoporosis Int., Suppl. 1, pp. S190-S193, (1993).
Okano et al, "Regulatory Activities of β-(3-Hydroxypropoxy)-1α,25-Dihydroxy-Vitamin D3, a Novel Synthetic Vitamin D3 Derivative, on Calcium Metabolism," Biochemical and Biophysical Research Communications, vol. 163 No. 3, pp. 1444-1449, (1989).
Ostrem et al, "24- and 26-homo-1,25-dihydroxyvitamin D3: Preferential activity in inducing differentiation of human leukemia cells HL-60 in vitro," Proc. Natl. Acad. Sci. USA, vol. 84, pp. 2610-2614, (1987).
Perlman et al, "1α,25-Dihydroxy-19-Nor-Vitamin D3. A Novel Vitamin D-Related Compound with Potential Therapeutic Activity," Tetrahedron Letters, vol. 31 No. 13, pp. 1823-1824, (1990).
Perlman et al, "Novel Synthesis of 19-Nor-Vitamin D Compounds," Tetrahedron Letters, vol. 32 No. 52, pp. 7663-7666, (1991).
Plum et al, "Biologically Active Noncalcemic Analogs of 1α,25-Dihydroxyvitamin D with an Abbreviated Side Chain Containing No Hydroxyl," PNAS, vol. 101 No. 18, pp. 6900-6904, (2004).
Posner et al, "Stereocontrolled Total Synthesis of Calcitriol Derivatives: 1,25-Dihydroxy-2-(4'-hydroxybutyl)vitamin D3 Analogs of an Osteoporosis Drug," Journal of Organic Chemistry, vol. 59 No. 25, pp. 7855-7861, (1994).
Posner et al, "2-Fluoroalkyl A-Ring Analogs of 1,25-Dihydroxyvitamin D3. Stereocontrolled Total Synthesis via Intramolecular and Intermolecular Diets—Alder Cycloadditions. Preliminary Biological Testing," Journal of Organic Chemistry, vol. 60 No. 14, pp. 4617-4628, (1995).

(Continued)

*Primary Examiner* — Sabiha N Qazi
(74) *Attorney, Agent, or Firm* — Andrus, Sceales, Starke & Sawall, LLP

(57) ABSTRACT

This invention discloses 2-methylene-(20S,25R)-19,26-dinor-vitamin D analogs, and specifically 2-methylene-(20S, 25R)-19,26-dinor-1α,25-dihydroxyvitamin $D_3$, and pharmaceutical uses therefor. This compound exhibits pronounced activity in arresting the proliferation of undifferentiated cells and inducing their differentiation to the monocyte thus evidencing use as an anti-cancer agent and for the treatment of skin diseases such as psoriasis as well as skin conditions such as wrinkles, slack skin, dry skin and insufficient sebum secretion. This compound also has little, if any, calcemic activity and therefore may be used to treat autoimmune disorders or inflammatory diseases in humans as well as renal osteodystrophy. This compound may also be used for the treatment or prevention of obesity.

90 Claims, 5 Drawing Sheets

(56) References Cited

OTHER PUBLICATIONS

Sardina et al, "Studies on the Synthesis of Side-Chain Hydroxylated Metabolites of Vitamin D. 2. Stereocontrolled Synthesis of 25-Hydroxyvitamin D2," J. Org. Chem., 51, pp. 1264-1269, (1986).

Sicinski et al, "New 1α,25-Dihydroxy-19-Norvitamin D3 Compounds of High Biological Activity: Synthesis and Biological Evaluation of 2-Hydroxymethyl, 2-Methyl, and 2-Methylene Analogues," Journal of Medical Chemistry, 41, pp. 4662-4674, (1998).

Sicinski et al, "New Highly Calcemic 1α,25-Dihydroxy-19-Norvitamin D3 Compounds with Modified Side Chain: 26,27-Dihomo- and 26,27-Dimethylene Analogs in 20S-Series," Steroids, vol. 67, pp. 247-256, (2002).

Toh et al, "Studies on a Convergent Route to Side-Chain Analogues of Vitamin D: 25-Hydroxy-23-Oxavitamin D3," J. Org. Chem., 48, 1414, (1983).

* cited by examiner

2-METHYLENE-(20S,25R)-19,26-DINOR-VITAMIN D ANALOGS

CROSS-REFERENCE TO RELATED APPLICATIONS

The present application claims the benefit of priority under 35 U.S.C. §119(e) to U.S. Provisional Application No. 61/017,226 filed on Dec. 28, 2007, the content of which is incorporated herein by reference in its entirety.

BACKGROUND OF THE INVENTION

This invention relates to vitamin D compounds, and more particularly to 2-methylene-(20S,25R)-19,26-dinor-vitamin D analogs and their pharmaceutical uses.

The natural hormone, $1\alpha,25$-dihydroxyvitamin $D_3$ and its analog in ergosterol series, i.e. $1\alpha,25$-dihydroxyvitamin $D_2$ are known to be highly potent regulators of calcium homeostasis in animals and humans, and their activity in cellular differentiation has also been established, Ostrem et al., Proc. Natl. Acad. Sci. USA, 84, 2610 (1987). Many structural analogs of these metabolites have been prepared and tested, including $1\alpha$-hydroxyvitamin $D_3$, $1\alpha$-hydroxyvitamin $D_2$, various side chain homologated vitamins and fluorinated analogs. Some of these compounds exhibit an interesting separation of activities in cell differentiation and calcium regulation. This difference in activity may be useful in the treatment of a variety of diseases such as renal osteodystrophy, vitamin D-resistant rickets, osteoporosis, psoriasis, and certain malignancies.

Another class of vitamin D analogs, i.e. the so called 19-nor-vitamin D compounds, is characterized by the replacement of the A-ring exocyclic methylene group (carbon 19), typical of the vitamin D system, by two hydrogen atoms. Biological testing of such 19-nor-analogs (e.g., $1\alpha,25$-dihydroxy-19-nor-vitamin $D_3$) revealed a selective activity profile with high potency in inducing cellular differentiation, and very low calcium mobilizing activity. Thus, these compounds are potentially useful as therapeutic agents for the treatment of malignancies, or the treatment of various skin disorders. Two different methods of synthesis of such 19-nor-vitamin D analogs have been described (Perlman et al., Tetrahedron Lett. 31, 1823 (1990); Perlman et al., Tetrahedron Lett. 32, 7663 (1991), and DeLuca et al., U.S. Pat. No. 5,086,191).

In U.S. Pat. No. 4,666,634, 2β-hydroxy and alkoxy (e.g., ED-71) analogs of $1\alpha,25$-dihydroxyvitamin $D_3$ have been described and examined by Chugai group as potential drugs for osteoporosis and as antitumor agents. See also Okano et al., Biochem. Biophys. Res. Commun. 163, 1444 (1989). Other 2-substituted (with hydroxyalkyl, e.g., ED-120, and fluoroalkyl groups) A-ring analogs of $1\alpha,25$-dihydroxyvitamin $D_3$ have also been prepared and tested (Miyamoto et al., Chem. Pharm. Bull. 41, 1111 (1993); Nishii et al., Osteoporosis Int. Suppl. 1, 190 (1993); Posner et al., J. Org. Chem. 59, 7855 (1994), and J. Org. Chem. 60, 4617 (1995)).

2-substituted analogs of $1\alpha,25$-dihydroxy-19-nor-vitamin $D_3$ have also been synthesized, i.e. compounds substituted at 2-position with hydroxy or alkoxy groups (DeLuca et al., U.S. Pat. No. 5,536,713), with 2-alkyl groups (DeLuca et al U.S. Pat. No. 5,945,410), and with 2-alkylidene groups (DeLuca et al. U.S. Pat. No. 5,843,928), which exhibit interesting and selective activity profiles. All these studies indicate that binding sites in vitamin D receptors can accommodate different substituents at C-2 in the synthesized vitamin D analogs.

In a continuing effort to explore the 19-nor class of pharmacologically important vitamin D compounds, analogs which are characterized by the presence of a methylene substituent at carbon 2 (C-2), a hydroxyl group at carbon 1 (C-1), and a shortened side chain attached to carbon 20 (C-20) have also been synthesized and tested. $1\alpha$-hydroxy-2-methylene-19-nor-pregnacalciferol is described in U.S. Pat. No. 6,566,352 while $1\alpha$-hydroxy-2-methylene-19-nor-homopregnacalciferol is described in U.S. Pat. Nos. 6,579,861 and $1\alpha$-hydroxy-2-methylene-19-nor-bishomopregnacalciferol is described in U.S. Pat. No. 6,627,622. All three of these compounds have relatively high binding activity to vitamin D receptors and relatively high cell differentiation activity, but little if any calcemic activity as compared to $1\alpha,25$-dihydroxyvitamin $D_3$. Their biological activities make these compounds excellent candidates for a variety of pharmaceutical uses, as set forth in the '352, '861 and '622 patents.

SUMMARY OF THE INVENTION

The present invention is directed toward 2-methylene-(20S,25R)-19,26-dinor-vitamin D analogs, their biological activity, and various pharmaceutical uses for these compounds. These new vitamin D compounds not known heretofore are the 19-nor-vitamin D analogs having a methylene group at the 2-position (C-2), a methyl group at the 20-position (C-20) in its S-configuration, the replacement of the methyl group typically located at the 26 position (C-26) in the side chain with a hydrogen atom, and the hydroxyl group at the 25-position (C-25) in its R-configuration. The preferred vitamin D analog is 2-methylene-(20S,25R)-19,26-dinor-$1\alpha$,25-dihydroxyvitamin $D_3$.

Structurally these 2-methylene-(20S,25R)-19,26-dinor-vitamin D analogs are characterized by the general formula I shown below:

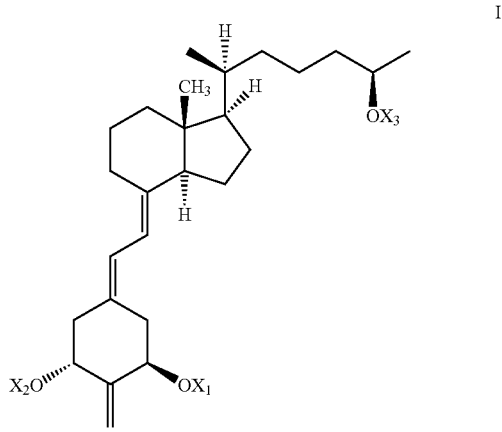

where $X_1$, $X_2$ and $X_3$, which may be the same or different, are each selected from hydrogen or a hydroxy-protecting group. The preferred analog is 2-methylene-(20S,25R)-19,26-dinor-$1\alpha$,25-dihydroxyvitamin $D_3$ which has the following formula Ia:

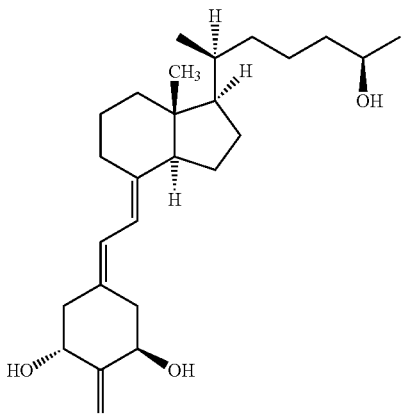

The above compounds I, particularly Ia, exhibit a desired, and highly advantageous, pattern of biological activity. These compounds are characterized by relatively high binding to vitamin D receptors. These compounds have some ability to promote intestinal calcium transport in vivo, in a dose dependent manner, but their ability would be classified as very low intestinal calcium transport activity, as compared to that of 1α,25-dihydroxyvitamin $D_3$. These compounds I, and particularly Ia, also have very low ability to mobilize calcium from bone, as compared to 1α,25-dihydroxyvitamin $D_3$. Hence, these compounds can be characterized as having little, if any, calcemic activity. It is undesirable to raise serum calcium to supraphysiologic levels when suppressing the pre-proparathyroid hormone gene (Darwish & DeLuca, Arch. Biochem. Biophys. 365, 123-130, 1999) and parathyroid gland proliferation. These analogs having little or no calcemic activity while very active on differentiation are expected to be useful as a therapy for suppression of secondary hyperparathyroidism as well as renal osteodystrophy.

The compounds I, particularly Ia, of the invention have also been discovered to be especially suited for treatment and prophylaxis of human disorders which are characterized by an imbalance in the immune system, e.g. in autoimmune diseases, including multiple sclerosis, lupus, diabetes mellitus, host versus graft rejection, and rejection of organ transplants; and additionally for the treatment of inflammatory diseases, such as rheumatoid arthritis, asthma, and inflammatory bowel diseases such as celiac disease, ulcerative colitis and Crohn's disease. Acne, alopecia and hypertension are other conditions which may be treated with the compounds of the invention.

The above compounds I, and particularly Ia, are also characterized by relatively high cell differentiation activity. Thus, these compounds also provide a therapeutic agent for the treatment of psoriasis, or as an anti-cancer agent, especially against leukemia, colon cancer, breast cancer, skin cancer and prostate cancer. In addition, due to their relatively high cell differentiation activity, these compounds provide a therapeutic agent for the treatment of various skin conditions including wrinkles, lack of adequate dermal hydration, i.e. dry skin, lack of adequate skin firmness, i.e. slack skin, and insufficient sebum secretion. Use of these compounds thus not only results in moisturizing of skin but also improves the barrier function of skin.

The compounds of the invention of formula I, and particularly formula Ia, are also useful in preventing or treating obesity, inhibiting adipocyte differentiation, inhibiting SCD-1 gene transcription, and/or reducing body fat in animal subjects. Therefore, in some embodiments, a method of preventing or treating obesity, inhibiting adipocyte differentiation, inhibiting SCD-1 gene transcription, and/or reducing body fat in an animal subject includes administering to the animal subject, an effective amount of one or more of the compounds or a pharmaceutical composition that includes one or more of the compounds of formula I. Administration of one or more of the compounds or the pharmaceutical compositions to the subject inhibits adipocyte differentiation, inhibits gene transcription, and/or reduces body fat in the animal subject.

One or more of the compounds may be present in a composition to treat the above-noted diseases and disorders in an amount from about 0.01 μg/gm to about 1000 μg/gm of the composition, preferably from about 0.1 μg/gm to about 500 μg/gm of the composition, and may be administered topically, transdermally, orally, rectally, nasally, sublingually or parenterally in dosages of from about 0.01 μg/day to about 1000 μg/day, preferably from about 0.1 μg/day to about 500 μg/day.

BRIEF DESCRIPTION OF THE DRAWINGS

In the drawings:

FIGS. 1-5 illustrate various biological activities of 2-methylene-(20S,25R)-19,26-dinor-1α,25-dihydroxyvitamin $D_3$, hereinafter referred to as "SR1," as compared to the native hormone 1α,25-dihydroxyvitamin $D_3$, hereinafter "1,25 $(OH)_2D_3$."

FIG. 1 is a graph illustrating the relative activity of SR1 and 1,25$(OH)_2D_3$ to compete for binding with [$^3$H]-1,25-$(OH)_2$-$D_3$ to the full-length recombinant rat vitamin D receptor;

FIG. 2 is a graph illustrating the percent HL-60 cell differentiation as a function of the concentration of SR1 and 1,25 $(OH)_2D_3$;

FIG. 3 is a graph illustrating the in vitro transcription activity of 1,25$(OH)_2D_3$ as compared to SR1;

Figure 1:
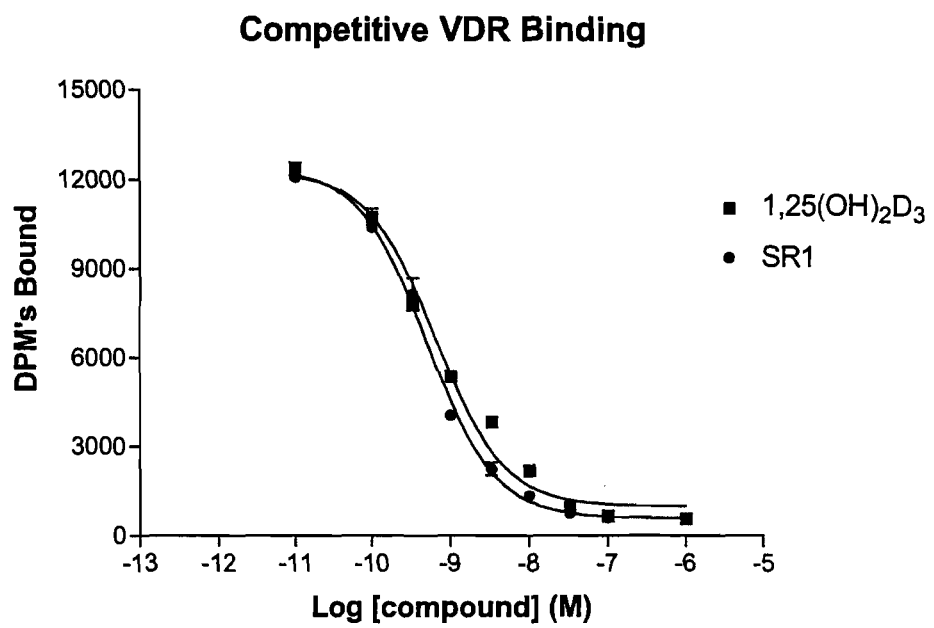

DETAILED DESCRIPTION OF THE INVENTION 2-methylene-(20S,25R)-19,26-dinor-1α,25-dihydroxyvitamin $D_3$ (referred to herein as "SR1") a 19-nor vitamin D analog which is characterized by the presence of a methylene substituent at the carbon 2 (C-2), a methyl group at the 20-position (C-20) in its S-configuration, the replacement of the methyl group typically located at the 26-position (C-26) in the side chain with a hydrogen atom, and the hydroxyl group at the 25-position (C-25) in its R-configuration, was synthesized and tested. Such vitamin D analog seemed an interesting target because the relatively small methylene group at the C-2 position should not interfere with binding to the vitamin D receptor. Structurally, this 19-nor analog is characterized by the general formula Ia previously illustrated herein, and its pro-drug (in protected hydroxy form) is characterized by general formula I previously illustrated herein.

The preparation of 2-methylene-(20S,25R)-19,26-dinor-vitamin D analogs having the structure I can be accomplished by a common general method, i.e. the condensation of a bicyclic Windaus-Grundmann type ketone II with the allylic phosphine oxide III to the corresponding 2-methylene-19,26-dinor-vitamin D analog IV followed by deprotection at C-1 and C-3 in the latter compound:

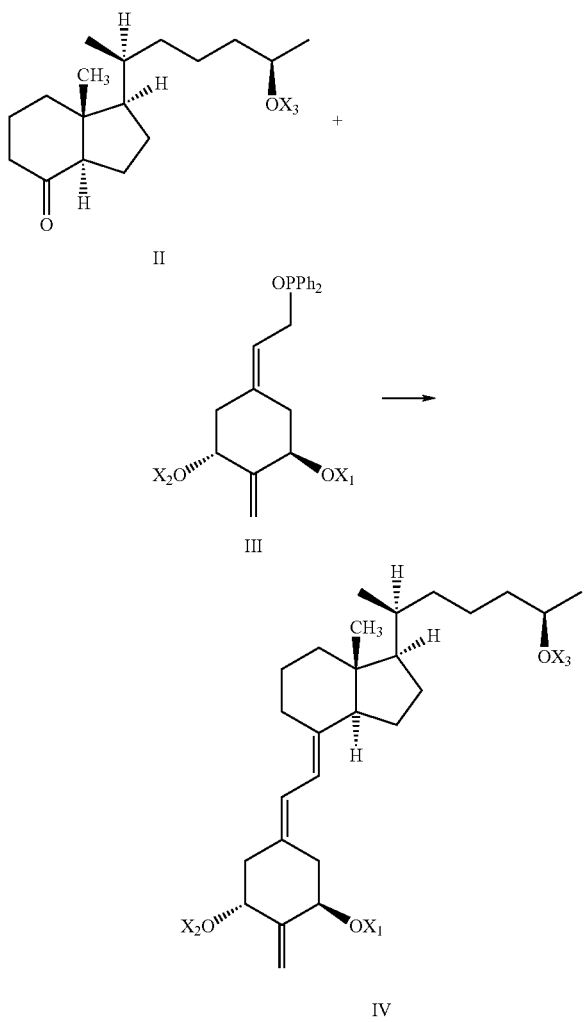

In the structures II, III and IV, groups $X_1$, $X_2$ and $X_3$ are hydroxy-protecting groups, preferably t-butyldimethylsilyl, it being also understood that any functionalities that might be sensitive, or that interfere with the condensation reaction, be suitably protected as is well-known in the art. The process shown above represents an application of the convergent synthesis concept, which has been applied effectively for the preparation of vitamin D compounds [e.g. Lythgoe et al., J. Chem. Soc. Perkin Trans. I, 590 (1978); Lythgoe, Chem. Soc. Rev. 9, 449 (1983); Toh et al., J. Org. Chem. 48, 1414 (1983); Baggiolini et al., J. Org. Chem. 51, 3098 (1986); Sardina et al., J. Org. Chem. 51, 1264 (1986); J. Org. Chem. 51, 1269 (1986); DeLuca et al., U.S. Pat. No. 5,086,191; DeLuca et al., U.S. Pat. No. 5,536,713].

The hydrindanone of the general structure II is not known. It can be prepared by the method shown in Schemes 1, 2 and 3 herein (see the preparation of compound SR1).

For the preparation of the required phosphine oxides of general structure III, a synthetic route has been developed starting from a methyl quinicate derivative which is easily obtained from commercial (1R,3R,4S,5R)-(−)-quinic acid as described by Perlman et al., Tetrahedron Lett. 32, 7663 (1991) and DeLuca et al., U.S. Pat. No. 5,086,191.

The overall process of the synthesis of compounds I and Ia is illustrated and described more completely in U.S. Pat. No. 5,843,928 entitled "2-Alkylidene-19-Nor-Vitamin D Compounds" the specification of which is specifically incorporated herein by reference.

As used in the description and in the claims, the term "hydroxy-protecting group" signifies any group commonly used for the temporary protection of hydroxy functions, such as for example, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groupings such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. The word "alkyl" as used in the description or the claims, denotes a straight-chain or branched alkyl radical of 1 to 10 carbons, in all its isomeric forms. Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group.

A "protected hydroxy" group is a hydroxy group derivatised or protected by any of the above groups commonly used for the temporary or permanent protection of hydroxy functions, e.g. the silyl, alkoxyalkyl, acyl or alkoxycarbonyl groups, as previously defined. The terms "hydroxyalkyl", "deuteroalkyl" and "fluoroalkyl" refer to an alkyl radical substituted by one or more hydroxy, deuterium or fluoro groups respectively.

More specifically, reference should be made to the following illustrative example and description as well as to Schemes 1-3 herein for a detailed illustration of the preparation of compound SR1.

In this example specific products identified by Arabic numerals (1, 2, 3) refer to the specific structures so identified in the Schemes 1, 2 and 3.

EXAMPLE

Chemistry. Ultraviolet (UV) absorption spectra were recorded with a Hitachi Model 60-100 UV-vis spectrometer in the solvent noted. $^1$H nuclear magnetic resonance (NMR) spectra were recorded at 500 MHz with a Bruker AM-500 FT spectrometer in deuteriochloroform. Chemical shifts (δ) are reported downfield from internal $Me_4Si$ (δ0.00). Mass spectra were recorded at 70 eV on a Kratos DS-50 TC instrument equipped with a Kratos MS-55 data system. Samples were introduced into the ion source maintained at 120-250° C. via a direct insertion probe. High-performance liquid chromatography (HPLC) was performed on a Waters Associates liquid chromatograph equipped with a Model 6000A solvent delivery system, a Model 6 UK Universal injector, a Model 486 tunable absorbance detector, and a differential R 401 refractometer.

Example 1

Preparation of (3R)-1-p-Toluenesulfonyloxy-3-triethylsilyloxy-butane (2)

To a stirred solution of the (R)-(−)-1,3-butanediol 1 (1 g, 11.1 mmol), DMAP (30 mg, 0.25 mmol) and Et$_3$N (4.6 mL, 3.33 g, 33 mmol) in anhydrous methylene chloride (20 mL) p-toluenesulfonyl chloride (2.54 g, 13.3 mmol) was added at 0° C. The reaction mixture was stirred at 4° C. for 22 h. Methylene chloride was added and the mixture was washed with water, dried (Na$_2$SO$_4$) and concentrated under reduced pressure. A residue was chromatographed on silica gel with hexane/ethyl acetate (8:2, then 1:1) to afford the tosylate (2.17 g, 80% yield) as a colorless oil.

To a stirred solution of the tosylate (2.17 g, 8.9 mmol) and 2,6-lutidine (1.14 mL, 1.05 g, 9.8 mmol) in anhydrous methylene chloride (15 mL) triethylsilyl trifluoromethanesulfonate (2 mL, 2.35 g, 8.9 mmol) was added at −50° C. The reaction mixture was allowed to warm to room temperature (4 h) and stirring was continued for additional 20 h. Methylene chloride was added and the mixture was washed with water, dried (Na$_2$SO$_4$) and concentrated under reduced pressure. A residue was chromatographed on silica gel with hexane/ethyl acetate (97:3) to afford the product 2 (3.16 g, 99% yield) as a colorless oil:

[α]$_D$ −20.7 (c 1.62, CHCl$_3$); $^1$H NMR (400 MHz, CDCl$_3$) δ 7.77 (2H, d, J=8.2 Hz, o-H$_{Ts}$), 7.33 (2H, d, J=8.2 Hz, m-H$_{Ts}$), 4.10 (2H, t, J=6.1 Hz, 1-H$_2$), 3.90 (1H, m, 3-H), 2.43 (3H, s, Me$_{Ts}$), 1.72 (2H, m, 2-H$_2$), 1.10 (3H, d, J=6.2 Hz, 4-H$_3$), 0.88 (9H, t, J=7.9 Hz, 3×SiCH$_2$CH$_3$), 0.50 (6H, q, J=7.9 Hz, 3×SiCH$_2$CH$_3$); $^{13}$C NMR (100 MHz) δ 144.62 (s, p-C$_{Ts}$), 133.02 (s, i-C$_{Ts}$), 129.72 (d, M-C$_{Ts}$), 127.82 (d, o-C$_{Ts}$), 67.78 (t, C-1), 64.45 (d, C-3), 38.46 (t, C-2), 23.81 (q, C-4), 21.51 (q, Me$_{Ts}$), 6.71 (q, SiCH$_2$CH$_3$), 4.76 (t, SiCH$_2$CH$_3$); MS (EI) m/z 359 (0.5, MH$^+$), 329 (59, M$^+$-C$_2$H$_5$), 285 (24), 258 (71), 229 (22), 212 (14), 199 (12), 159 (28), 145 (45), 115 (72), 91 (100); exact mass calculated for C$_{15}$H$_{25}$O$_4$SSi (M$^+$-C$_2$H$_5$) 329.1243, found 329.1248.

Preparation of (3R)-1-Iodo-3-triethylsilyloxy-butane (3)

To a stirred solution of the tosylate 2 (3.15 g, 8.8 mmol) in anhydrous acetone (50 mL) potassium iodide (8 g, 48 mmol) was added and the reaction mixture was refluxed for 10 h. Water (30 mL) was added and the solution was extracted with ethyl acetate. The combined organic phases were dried (Na$_2$SO$_4$) and concentrated under reduced pressure. The residue was chromatographed on silica gel with hexane/ethyl acetate (97:3) to give the alcohol 3 (2.6 g, 94% yield) as a colorless oil:

[α]$_D$ −39.5 (c 1.75, CHCl$_3$); $^1$H NMR (400 MHz, CDCl$_3$) δ 3.89 (1H, m, 3-H), 3.22 (2H, t, J=7.0 Hz, 1-H$_2$), 1.91 (2H, m, 2-H$_2$), 1.16 (3H, d, J=6.1 Hz, 4-H$_3$), 0.96 (9H, t, J=7.9 Hz, 3×SiCH$_2$CH$_3$), 0.61 (6H, q, J=7.9 Hz, 3×SiCH$_2$CH$_3$); $^{13}$C NMR (100 MHz) δ 68.14 (d, C-3), 43.24 (t, C-2), 23.46 (q, C-4), 6.87 (q, SiCH$_2$CH$_3$), 5.00 (t, SiCH$_2$CH$_3$), 3.37 (t, C-1); MS (EI) m/z 314 (1, M$^+$), 299 (3, M$^+$-CH$_3$), 285 (100, M$^+$-C$_2$H$_5$), 257 (78, M$^+$-C$_4$H$_9$), 228 (56), 212 (99), 184 (65), 157 (70), 129 (46), 115 (46); exact mass calculated for C$_8$H$_{18}$OISi (M$^+$-C$_2$H$_5$) 285.0172, found 285.0167.

Preparation of (3R)-Hydroxybutyl-triphenylphosphonium iodide (4)

To a stirred solution of the iodide 3 (1.24 g, 3.9 mmol) in acetonitrile (50 mL) triphenylphosphine (3.1 g, 11.8 mmol) was added and the reaction mixture was refluxed for 2 days. Acetonitrile was evaporated under reduced pressure, ethyl acetate (50 mL) was added and the mixture was stirred at room temperature for 4 h. After removal of the solvent by filtration the solid was washed with ethyl acetate, filtered off and dried. The pure phosphonium salt 4 (1.74 g, 96% yield) was obtained as white crystals:

$^1$H NMR (400 MHz, CD$_3$OD) δ 8.00-7.70 (15H, m, H$_{Ph}$), 3.89 (1H, m, 3-H), 3.48 (2H, m, 1-H$_2$), 1.73 (2H, m, 2-H$_2$), 1.19 (3H, d, J=6.2 Hz, 4-H$_3$); $^{13}$C NMR (100 MHz) δ 136.41 (d, p-C$_{Ph}$), 134.99 (d, J$_{C-P}$=10.1 Hz, m-C$_{Ph}$), 131.70 (d, J$_{C-P}$=12.1 Hz, O—C$_{Ph}$), 120.03 (s, J$_{C-P}$=86.5 Hz, i-C$_{Ph}$), 67.94 (d, J$_{C-P}$=17.1 Hz, C-3), 32.52 (t, J$_{C-P}$=4.0 Hz, C-2), 23.38 (q, C-4), 19.85 (t, J$_{C-P}$=54.3 Hz, C-1); exact mass calculated for C$_{22}$H$_{24}$OPI (M$^+$) 335.1565, found 335.1562.

Preparation of (8S,20S)-des-A,B-20-(hydroxymethyl)pregnan-8-ol (5)

Ozone was passed through a solution of vitamin D$_2$ (3 g, 7.6 mmol) in methanol (250 mL) and pyridine (2.44 g, 2.5 mL, 31 mmol) for 50 min at −78° C. The reaction mixture was then flushed with an oxygen for 15 min to remove the residual ozone and the solution was treated with NaBH$_4$ (0.75 g, 20 mmol). After 20 min the second portion of NaBH$_4$ (0.75 g, 20 mmol) was added and the mixture was allowed to warm to room temperature. The third portion of NaBH$_4$ (0.75 g, 20 mmol) was then added and the reaction mixture was stirred for 18 h. The reaction was quenched with water (40 mL) and the solution was concentrated under reduced pressure. The residue was extracted with ethyl acetate and the combined organic phases were washed with 1M aq. HCl, saturated aq. NaHCO$_3$, dried (Na$_2$SO$_4$) and concentrated under reduced pressure. The residue was chromatographed on silica gel with hexane/ethyl acetate (75:25) to give the diol 5 (1.21 g, 75% yield) as white crystals:

m.p. 106-108° C.; [α]$_D$ +30.2° (c 1.46, CHCl$_3$); $^1$H NMR (400 MHz, CDCl$_3$) δ 4.08 (1H, d, J=2.0 Hz, 8α-H), 3.63 (1H, dd, J=10.5, 3.1 Hz, 22-H), 3.38 (1H, dd, J=10.5, 6.8 Hz, 22-H), 1.99 (1H, br.d, J=13.2 Hz), 1.03 (3H, d, J=6.6 Hz, 21-H$_3$), 0.956 (3H, s, 18-H$_3$); $^{13}$C NMR (100 MHz) δ 69.16 (d, C-8), 67.74 (t, C-22), 52.90 (d), 52.33 (d), 41.83 (s, C-13), 40.19 (t), 38.20 (d), 33.53 (t), 26.62 (t), 22.54 (t), 17.36 (t), 16.59 (q, C-21), 13.54 (q, C-18); MS (EI) m/z 212 (2, M$^+$), 194 (34, M$^+$-H$_2$O), 179 (33, M$^+$-H$_2$O—CH$_3$), 163 (18, M$^+$-CH$_2$OH—H$_2$O), 135 (36), 125 (54), 111 (100), 95 (63), 81 (67); exact mass calculated for C$_{13}$H$_{22}$O (M$^+$-H$_2$O) 194.1671, found 194.1665.

Preparation of (8S,20S)-des-A,B-8-benzoyloxy-20-(hydroxymethyl)pregnane (6)

Benzoyl chloride (2.4 g, 2 mL, 17 mmol) was added to a solution of the diol 5 (1.2 g, 5.7 mmol) and DMAP (30 mg, 0.2 mmol) in anhydrous pyridine (20 mL) at 0° C. The reaction mixture was stirred at 4° C. for 24 h, diluted with methylene chloride (100 mL), washed with 5% aq. HCl, water, saturated aq. NaHCO$_3$, dried (Na$_2$SO$_4$) and concentrated under reduced pressure. The residue (3.39 g) was treated with a solution of KOH (1g, 15.5 mmol) in anhydrous ethanol (30 mL) at room temperature. After stirring of the reaction mixture for 3 h, ice and 5% aq. HCl were added until pH=6. The solution was extracted with ethyl acetate (3×50 mL) and the combined organic phases were washed with saturated aq. NaHCO$_3$, dried (Na$_2$SO$_4$) and concentrated under reduced pressure. The residue was chromatographed on silica gel with hexane/ethyl acetate (75:25) to give the alcohol 6 (1.67 g, 93% yield) as a colorless oil:

[α]$_D$+56.0 (c 0.48, CHCl$_3$); $^1$H NMR (400 MHz, CDCl$_3$+TMS) δ 8.08-8.02 (2H, m, o-H$_{Bz}$), 7.59-7.53 (1H, m, p-H$_{Bz}$), 7.50-7.40 (2H, m, m-H$_{Bz}$), 5.42 (1H, d, J=2.4 Hz, 8α-H), 3.65 (1H, dd, J=10.5, 3.2 Hz, 22-H), 3.39 (1H, dd, J=10.5, 6.8 Hz, 22-H), 1.08 (3H, d, J=5.3 Hz, 21-H$_3$), 1.07 (3H, s, 18-H$_3$); $^{13}$C NMR (125 MHz) δ 166.70 (s, C=O), 132.93 (d, p-C$_{Bz}$), 130.04 (s, i-C$_{Bz}$), 129.75 (d, o-C$_{Bz}$), 128.57 (d, m-C$_{Bz}$), 72.27 (d, C-8), 67.95 (t, C-22), 52.96 (d), 51.60 (d), 42.15 (s, C-13), 39.98 (t), 38.61 (d), 30.73 (t), 26.81 (t), 22.91 (t), 18.20 (t), 16.87 (q, C-21), 13.81 (q, C-18); MS (EI) m/z 316 (5, M$^+$), 301 (3, M$^+$-Me), 299 (1, M$^+$-OH), 298 (2, M$^+$-H$_2$O), 285 (10, M$^+$-CH$_2$OH), 257 (6), 230 (9), 194 (80), 135 (84), 105 (100); exact mass calculated for C$_{20}$H$_{28}$O$_3$ 316.2038, found 316.2019.

Preparation of (8S,20S)-des-A,B-8-benzoyloxy-20-formylpregnane (7)

Sulfur trioxide pyridine complex (1.94 g, 12.2 mmol) was added to a solution of the alcohol 6 (640 mg, 2.03 mmol), triethylamine (1.41 mL, 1.02 g, 10.1 mmol) in anhydrous methylene chloride (10 mL) and anhydrous DMSO (2 mL) at 0° C. The reaction mixture was stirred under argon at 0° C. for 1 h and then concentrated. The residue was diluted with ethyl acetate, washed with brine, dried (Na$_2$SO$_4$) and concentrated. The residue was purified by column chromatography on silica gel with hexane/ethyl acetate (95:5) to give the aldehyde 7 (529 mg, 83% yield) as an oil:

$^1$H NMR (400 MHz, CDCl$_3$+TMS) δ 9.60 (1H, d, J=3.1 Hz, CHO), 8.05 (2H, m, o-H$_{Bz}$), 7.57 (1H, m, p-H$_{Bz}$), 7.45 (2H, m, m-H$_{Bz}$), 5.44 (1H, s, 8α-H), 2.39 (1H, m, 20-H), 2.03 (2H, dm, J=11.5 Hz), 1.15 (3H, d, J=6.9 Hz, 21-H$_3$), 1.10 (3H, s, 18-H$_3$); $^{13}$C NMR (100 MHz) δ 204.78 (d, CHO), 166.70 (s, C=O), 132.78 (d, p-Bz), 130.69 (s, i-Bz), 129.50 (d, o-Bz), 128.38, (d, m-Bz), 71.66 (d, C-8), 51.30 (d), 50.95 (d), 49.20 (d), 42.38 (s, C-13), 39.62 (t), 30.47 (t), 25.99 (t), 22.92 (t), 17.92 (t), 13.90 (q), 13.35 (q); MS (EI) m/z 314 (1, M$^+$), 299 (0.5, M$^+$-Me), 286 (1, M$^+$-CO), 285 (5, M$^+$-CHO), 257 (1, M$^+$-C$_3$H$_5$O), 209 (10, M$^+$-PhCO), 192 (38), 134 (60), 105 (100), 77 (50); exact mass calculated for C$_{20}$H$_{26}$O$_3$ 314.1882, found 314.1887.

Preparation of (8S,20R)-des-A,B-8-benzoyloxy-20-(hydroxymethyl)pregnane (8)

The aldehyde 7 (364 mg, 1.12 mmol) was dissolved in methylene chloride (15 mL) and a 40% aq. n-Bu$_4$NOH solution (1.47 mL, 1.45 g, 2.24 mmol) was added. The resulting mixture was stirred under argon at room temperature for 16 h, diluted with methylene chloride (20 mL), washed with water, dried (Na$_2$SO$_4$) and concentrated under reduced pressure. A residue was chromatographed on silica gel with hexane/ethyl acetate (95:5) to afford a mixture of aldehyde 7 and its 20-epimer (292 mg, 80% yield) in ca. 1:2 ratio (by $^1$H NMR).

This mixture of aldehydes (292 mg, 0.9 mmol) was dissolved in THF (5 mL) and NaBH$_4$ (64 mg, 1.7 mmol) was added, followed by a dropwise addition of ethanol (5 mL). The reaction mixture was stirred at room temperature for 30 min and it was quenched with a saturated aq. NH$_4$Cl solution. The mixture was extracted with ether (3×20 mL) and the combined organic phase was washed with water, dried (Na$_2$SO$_4$) and concentrated under reduced pressure. The residue was chromatographed on silica gel with hexane/ethyl acetate (96:4→80:20) to give the desired, pure (20R)-alcohol 8 (160 mg, 55% yield) as an oil and a mixture of 8 and its 20-epimer 6 (126 mg, 43% yield) in ca. 1:3 ratio (by $^1$H NMR).

[α]$_D$+50.1 (c 1.09, CHCl$_3$); $^1$H NMR (400 MHz, CDCl$_3$+TMS) δ 8.05 (2H, m, o-H$_{Bz}$), 7.55 (1H, m, p-H$_{Bz}$), 7.44 (2H, m, m-H$_{Bz}$), 5.41 (1H, s, 8α-H), 3.77 (1H, dd, J=10.4, 3.3 Hz, 22-H), 3.45 (1H, dd, J=10.4, 7.4 Hz, 22-H), 1.067 (3H, s, 18-H$_3$), 0.973 (3H, d, J=6.6 Hz, 21-H$_3$); $^{13}$C NMR (100 MHz) δ 166.36 (s, C=O), 132.61 (d, p-C$_{Bz}$), 130.63 (s, i-C$_{Bz}$), 129.39 (d, o-C$_{Bz}$), 128.23 (d, m-C$_{Bz}$), 71.97 (d, C-8), 66.42 (t, C-22), 52.65 (d), 51.38 (d), 41.58 (s, C-13), 39.16 (t), 37.45 (d), 30.38 (t), 26.29 (t), 22.35 (t), 17.89 (t), 16.42 (q, C-21), 13.78 (q, C-18); MS (EI) m/z 316 (16, M$^+$), 301 (5, M$^+$-Me), 299 (2, M$^+$-OH), 298 (3, M$^+$-H$_2$O), 285 (9, M$^+$-CH$_2$OH), 257 (5), 242 (11), 230 (8), 194 (60), 147 (71), 105 (100); exact mass calculated for C$_{20}$H$_{28}$O$_3$ 316.2038, found 316.2050.

Preparation of (8S,20R)-des-A,B-8-benzoyloxy-20-formylpregnane (9)

Sulfur trioxide pyridine complex (258 mg, 1.62 mmol) was added to a solution of the alcohol 8 (85 mg, 0.27 mmol), triethylamine (188 μL, 136 mg, 1.35 mmol) in anhydrous methylene chloride (5 mL) and anhydrous DMSO (1 mL) at 0° C. The reaction mixture was stirred under argon at 0° C. for 1 h and then concentrated. The residue was diluted with ethyl acetate, washed with brine, dried (Na$_2$SO$_4$) and concentrated. The residue was purified by column chromatography on silica gel with hexane/ethyl acetate (95:5) to give the aldehyde 9 (70 mg, 83% yield) as an oil:

[α]$_D$+28.8 (c 0.88, CHCl$_3$); $^1$H NMR (500 MHz, CDCl$_3$) δ 9.55 (1H, d, J=5.0 Hz, CHO), 8.02 (2H, m, o-H$_{Bz}$), 7.54 (1H, m, p-H$_{Bz}$), 7.43 (2H, m, m-H$_{Bz}$), 5.42 (1H, s, 8α-H), 2.35 (1H, m, 20-H), 2.07 (1H, m), 1.87 (1H, m), 1.05 (3H, s, 18-H$_3$), 1.04 (3H, d, J=7.8 Hz, 21-H$_3$); $^{13}$C NMR (125 MHz) δ 205.51 (d, CHO), 166.34 (s, C=O), 132.76 (d, p-C$_{Bz}$), 130.62 (s, i-C$_{Bz}$), 129.47 (d, o-C$_{Bz}$), 128.35, (d, m-C$_{Bz}$), 71.52 (d, C-8), 52.08 (d), 51.08 (d), 48.40 (d), 41.55 (s, C-13), 38.54 (t), 30.41 (t), 25.28 (t), 22.08 (t), 17.68 (t), 14.49 (q), 13.38 (q); MS (EI) m/z 314 (2, M$^+$), 285 (3, M$^+$-CHO), 209 (8, M$^+$-PhCO), 192 (30, M$^+$-PhCOOH), 177 (14), 134 (45), 105 (100), 77 (50); exact mass calculated for C$_{19}$H$_{25}$O$_2$ (M$^+$-CHO) 285.1855, found 285.1849.

Preparation of (8S,20S)-des-A,B-8-benzoyloxy-20-[(4R)-hydroxy-pent-(1E)-en-yl]pregnane (10)

To a stirred suspension of the phosphonium salt 4 (221 mg, 0.66 mmol) in anhydrous THF (5 mL) butyllithium (1.6 M, 720 μL, 1.15 mmol) was added at −20° C. The solution turned deep orange. After 1 h a precooled (−20° C.) solution of the aldehyde 9 (70 mg, 0.22 mmol) in anhydrous THF (2 mL) was added and the reaction mixture was stirred at −20° C. for 3 h and at room temperature for 18 h. The reaction was quenched with water and the mixture was extracted with ethyl acetate. Combined organic phases were washed with brine, dried (Na$_2$SO$_4$) and evaporated. The residue was chromatographed on silica gel with hexane/ethyl acetate (95:5) to give the product 10 (39 mg, 48% yield):

[α]$_D$−28.8 (c 0.8, CHCl$_3$); $^1$H NMR (400 MHz, CDCl$_3$) δ 8.05 (2H, m, o-H$_{Bz}$), 7.55 (1H, m, p-H$_{Bz}$), 7.44 (2H, m, m-H$_{Bz}$), 5.41 (1H, s, 8α-H), 5.50-5.30 (2H, m, 22-H and 23-H), 3.84 (1H, m, 25-H), 1.20 (3H, d, J=6.2 Hz, 27-H$_3$), 1.04 (3H, s, 18-H$_3$), 0.93 (3H, d, J=6.6 Hz, 21-H$_3$); $^{13}$C NMR (100 MHz) δ 166.45 (s, C=O), 140.74 (d, C-22), 132.67 (d, p-C$_{Bz}$), 130.86 (s, i-C$_{Bz}$), 129.53 (d, o-C$_{Bz}$), 128.32 (d, m-C$_{Bz}$), 123.33 (d, C-23), 72.08 (d, C-8), 67.70 (d, C-25), 56.33 (d), 51.48 (d), 42.46 (t), 41.94 (s, C-13), 40.16 (d), 39.48 (t), 30.60 (t), 26.86 (t), 22.74 (q, C-27), 22.50 (t), 21.46 (q, C-21), 17.81 (t), 13.89 (q, C-18); MS (EI) m/z 370 (8, M$^+$), 355 (1, M$^+$-CH$_3$), 326 (2, M$^+$-C$_2$H$_4$O), 284 (12, M$^+$-C$_5$H$_{10}$O), 265 (2, M$^+$-PhCO), 248 (28, M$^+$-PhCOOH), 230 (9), 204 (14), 189 (10), 162 (63), 135 (71), 105 (100); exact mass calculated for C$_{24}$H$_{34}$O$_3$Na (MNa$^+$) 393.2406, found 393.2407.

Preparation of (8S,20S)-des-A,B-8-benzoyloxy-20-[(4R)-hydroxy-pentyl]pregnane (11)

A solution of the compound 10 (39 mg, 0.11 mmol) in methanol (6 mL) was hydrogenated for 17 h in the presence of 10% palladium on powdered charcoal (6 mg). The reaction mixture was filtered through a bed of Celite with several methanol washes, the filtrate was concentrated and the residue was chromatographed on silica gel with hexane/ethyl acetate (95:5) to give the product 11 (27 mg, 66% yield):
[α]$_D$+18.5 (c 1.0, CHCl$_3$); $^1$H NMR (500 MHz, CDCl$_3$+TMS) δ 8.05 (2H, m, o-H$_{Bz}$), 7.56 (1H, m, p-H$_{Bz}$), 7.44 (2H, m, m-H$_{Bz}$), 5.41 (1H, d, J=1.8 Hz, 8α-H), 3.80 (1H, m, 25-H), 2.02 (2H, m), 1.81 (2H, m), 1.20 (3H, d, J=6.2 Hz, 27-H$_3$), 1.04 (3H, s, 18-H$_3$), 0.84 (3H, d, J=6.6 Hz, 21-H$_3$); $^{13}$C NMR (125 MHz) δ 166.48 (s, C=O), 132.67 (d, p-C$_{Bz}$), 130.87 (s, i-C$_{Bz}$), 129.53 (d, o-C$_{Bz}$), 128.33 (d, m-C$_{Bz}$), 72.22 (d, C-8), 68.19 (d, C-25), 55.99 (d), 51.63 (d), 41.95 (s, C-13), 39.85 (t), 39.67 (t), 35.19 (t), 34.83 (d), 30.53 (t), 26.94 (t), 23.57 (q, C-27), 22.52 (t), 22.39 (t), 18.47 (q, C-21), 18.06 (t), 13.81 (q, C-18); MS (EI) m/z 372 (12, M$^+$), 354 (3, M$^+$-H$_2$O), 339 (0.5, M$^+$-H$_2$O—CH$_3$), 327 (0.5, M$^+$-C$_2$H$_5$O), 285 (1, M$^+$-C$_5$H$_{11}$O), 267 (5, M$^+$-PhCO), 250 (60, M$^+$-PhCOOH), 232 (24), 163 (24), 135 (63), 105 (100); exact mass calculated for C$_{24}$H$_{36}$O$_3$Na (MNa$^+$) 395.2562, found 395.2567.

Preparation of (8S,20S)-des-A,B-8-benzoyloxy-20-[(4R)-tert-butyldimethylsilyloxy-pentyl]pregnane (12)

tert-Butyldimethylsilyl trifluoromethanesulfonate (32 μL, 37 mg, 0.14 mmol) was added to a solution of the alcohol 11 (27 mg, 0.07 mmol) and 2,6-lutidine (33 μL, 30 mg, 0.28 mmol) in anhydrous methylene chloride (3 mL) at −20° C. The mixture was stirred under argon at 0° C. for 1 h. The reaction was quenched with water and extracted with methylene chloride. The combined organic phases were washed with brine, dried (Na$_2$SO$_4$) and concentrated under reduced pressure. The residue was chromatographed on silica gel with hexane and hexane/ethyl:acetate (97:3) to give the product 12 (34 mg, 100%):
[α]$_D$+10.8 (c 1.3, CHCl$_3$); $^1$H NMR (400 MHz, CDCl$_3$+TMS) δ 8.04 (2H, m, o-H$_{Bz}$), 7.54 (1H, m, p-H$_{Bz}$), 7.43 (2H, m, m-H$_{Bz}$), 5.40 (1H, s, 8α-H), 3.77 (1H, m, 25-H), 2.01 (2H, m), 1.80 (2H, m), 1.11 (3H, d, J=6.0 Hz, 27-H$_3$), 1.03 (3H, s, 18-H$_3$), 0.88 (9H, s, Si-t-Bu), 0.82 (3H, d, J=6.5 Hz, 21-H$_3$), 0.04 (6H, s, SiMe$_2$); $^{13}$C NMR (100 MHz) δ 166.50 (s, C=O), 132.66 (d, p-C$_{Bz}$), 130.91 (s, i-C$_{Bz}$), 129.55 (d, o-C$_{Bz}$), 128.33 (d, m-C$_{Bz}$), 72.26 (d, C-8), 68.72 (d, C-25), 56.02 (d), 51.67 (d), 41.97 (s, C-13), 40.09 (t), 39.85 (t), 35.32 (t), 34.86 (d), 30.58 (t), 26.94 (t), 25.92 (q, SiCMe$_3$), 23.87 (q, C-27), 22.56 (t), 22.36 (t), 18.49 (q, C-21), 18.$\overline{18}$ (s, SiCMe$_3$), 18.07 (t), 13.80 (q, C-18), −4.38 (q, Si$\underline{Me}$), −4.68 (q, $\overline{Si}$Me); MS (EI) m/z 485 (2, M$^+$-H), 471 (2, M$^+$-CH$_3$), 307 (15, M$^+$-PhCOOH—C$_4$H$_9$), 233 (86, M$^+$-PhCOOH-t-BuSiMe$_2$O), 197 (87), 180 (86), 163 (100), 135 (74), 123 (80), 109 (89); exact mass calculated for C$_{30}$H$_{50}$O$_3$SiNa (MNa$^+$) 509.3427, found 509.3437.

Preparation of (8S,20S)-des-A,B-20-[(4R)-tert-butyldimethylsilyloxy-pentyl]pregnan-8-ol (13)

A solution of sodium hydroxide in ethanol (2.5M, 2 mL) was added to a stirred solution of the benzoate 12 (34 mg, 70 μmol) in anhydrous ethanol (6 mL) and the reaction mixture was refluxed for 18 h. The mixture was cooled to room temperature, neutralized with 5% aq. HCl and extracted with dichloromethane. Combined organic phases were washed with saturated aq. NaHCO$_3$, dried (Na$_2$SO$_4$) and evaporated. The residue was chromatographed on silica gel with hexane/ethyl acetate (95:5) to give the alcohol 13 (20 mg, 74% yield):
[α]$_D$+8.1 (c 0.75, CHCl$_3$); $^1$H NMR (400 MHz, CDCl$_3$) δ 4.07 (1H, d, J=1.8 Hz, 8α-H), 3.77 (1H, m, 25-H), 1.96 (1H, m), 1.81 (3H, m), 1.11 (3H, d, J=6.1 Hz, 27-H$_3$), 0.92 (3H, s, 18-H$_3$), 0.88 (9H, s, Si-t-Bu), 0.81 (3H, d, J=6.6 Hz, 21-H$_3$), 0.04 (6H, s, SiMe$_2$); $^{13}$C NMR (100 MHz) δ 69.45 (d, C-8), 68.71 (d, C-25), 56.23 (d), 52.65 (d), 41.89 (s, C-13), 40.28 (t), 40.08 (t), 35.26 (t), 34.72 (d), 33.56 (t), 27.04 (t), 25.91 (q, SiCMe$_3$), 23.84 (q, C-27), 22.42 (t), 22.31 (t), 18.50 (q, C-21), 18.$\overline{16}$ (s, SiCMe$_3$), 17.46 (t), 13.75 (q, C-18), −4.39 (q, Si Me), −4.69 (q, SiMe); MS (EI) m/z 382 (2, M$^+$), 367 (6, $\overline{M}$$^+$-CH$_3$), 325 (13, $\overline{M}$$^+$-C$_4$H$_9$), 307 (4, M$^+$-C$_4$H$_9$—H$_2$O), 233 (57), 191 (44), 177 (50), 163 (60) 151 (53), 135 (55), 123 (58), 93 (65), 75 (100); exact mass calculated for C$_{19}$H$_{37}$O$_2$Si (M$^+$-C$_4$H$_9$) 325.2563, found 325.2573.

Preparation of (20S)-des-A,B-20-[(4R)-tert-butyldimethylsilyloxy-pentyl]pregnan-8-one (14)

Molecular sieves A4 (60 mg) were added to a solution of 4-methylmorpholine (20 mg, 0.2 mmol) in dichloromethane (0.5 mL). The mixture was stirred at room temperature for 15 min and tetrapropylammonium perruthenate (3 mg, 9 μmol) was added, followed by a solution of alcohol 13 (20 mg, 52 μmol) in dichloromethane (300+300 μL). The resulting suspension was stirred at room temperature for 1 h. The reaction mixture was filtered through a Waters silica Sep-Pak cartridge (5 g) that was further washed with dichloromethane. After removal of the solvent the ketone 14 (19 mg, 96% yield) was obtained as a colorless oil:
[α]$_D$−33.7 (c 0.7, CHCl$_3$); $^1$H NMR (400 MHz, CDCl$_3$) δ 3.76 (1H, m, 25-H), 2.44 (1H, dd, J=11.4, 7.7 Hz), 1.12 (3H, d, J=6.0 Hz, 27-H$_3$), 0.89 (9H, s, Si-t-Bu), 0.84 (3H, d, J=5.9 Hz, 21-H$_3$), 0.63 (3H, s, 18-H$_3$), 0.05 (6H, s, SiMe$_2$); $^{13}$C NMR (100 MHz) δ 212.13 (s), 68.64 (d, C-25), 62.02 (d), 56.19 (d), 49.94 (s, C-13), 40.96 (t), 40.03 (t), 38.84 (t), 35.52 (t), 34.84 (d), 27.13 (t), 25.89 (q, SiCMe$_3$), 24.03 (t), 23.84 (q, C-27), 22.27 (t), 18.93 (t), 18.45 (q, $\overline{C-21}$), 18.16 (s, SiCMe$_3$), 12.70 (q, C-18), −4.38 (q, SiMe), −4.70 (q, SiMe); $\overline{MS}$ (EI) m/z 380 (4, M$^+$), 379 (5, M$^+$-$\overline{H}$), 365 (19, M$^+$-$\overline{CH}$$_3$), 351 (7, M$^+$-C$_2$H$_5$), 323 (100, M$^+$-C$_4$H$_8$), 231 (87), 189 (64), 175 (60), 161 (75), 149 (70), 135 (97), 121 (65), 95 (81); exact mass calculated for C$_{22}$H$_{41}$O$_2$Si (M$^+$-CH$_3$) 365.2876, found 365.2880.

Preparation of (20S,25R)-2-Methylene-19,26-dinor-1α,25-dihydroxyvitamin D$_3$ (17)

To a solution of phosphine oxide 15 (74 mg, 127 μmol) in anhydrous THF (400 μL) at −20° C. was slowly added PhLi (1.8 M in di-n-butylether, 100 μL, 180 μmol) under argon with stirring. The solution turned deep orange. After 30 min the mixture was cooled to −78° C. and a precooled (−78° C.) solution of ketone 14 (19 mg, 50 μmol) in anhydrous THF (200+100 μL) was slowly added. The mixture was stirred under argon at −78° C. for 3 h and at 0° C. for 18 h. Ethyl acetate was added, and the organic phase was washed with brine, dried (Na$_2$SO$_4$) and evaporated. The residue was dissolved in hexane and applied on a Waters silica Sep-Pak cartridge (2 g). The cartridge was washed with hexane and hexane/ethyl acetate (99.5:0.5) to give 19-norvitamin derivative 16 (33 mg, 89% yield). Then the Sep-Pak was washed with ethyl acetate to recover diphenylphosphine oxide 15 (48 mg). For analytical purpose a sample of the protected vitamin 16 was further purified by HPLC (9.4×250 mm Zorbax Sil column, 4 mL/min, hexane/2-propanol (99.9:0.1) solvent system, R$_t$=3.45 min):

UV (in hexane) λ$_{max}$262.6, 253.0, 244.8 nm; $^1$H NMR (500 MHz, CDCl$_3$) δ 6.22 and 5.84 (each 1H, each d, J=11.2 Hz, 6- and 7-H), 4.97 and 4.92 (each 1H, each s, =CH$_2$), 4.43 (2H, m, 1β- and 3α-H), 3.77 (1H, m, 25-H), 2.83 (1H, dm, J=12.6 Hz, 9β-H), 2.51 (1H, dd, J=13.3, 6.0 Hz, 10α-H), 2.46 (1H, dd, J=12.6, 4.5 Hz, 4α-H), 2.34 (1H, dd, J=13.3, 2.9 Hz, 10β-H), 2.18 (1H, dd, J=12.6, 8.3 Hz, 4β-H), 1.99 (2H, m), 1.87 (1H, m), 1.12 (3H, d, J=6.1 Hz, 27-H$_3$), 0.899 (9H, s, Si-t-Bu), 0.892 (9H, s, Si-t-Bu), 0.867 (9H, s, Si-t-Bu), 0.84 (3H, d, J=6.5 Hz, 21-H$_3$), 0.541 (3H, s, 18-H$_3$), 0.082 (3H, s, SiMe), 0.068 (3H, s, SiMe), 0.052 (9H, s, 3×SiMe), 0.028 (3H, s, SiMe); $^{13}$C NMR (125 MHz) δ 152.99 (s, C-2), 141.22 (s, C-8), 132.71 (s, C-5), 122.42 (d, C-6), 116.11 (d, C-7), 106.25 (t, =CH$_2$), 72.52 and 71.65 (each d, C-1 and C-3), 68.74 (d, C-25), 56.32 (d), 56.19 (d), 47.61 (t), 45.70 (s, C-13), 40.50 (t), 40.12 (t), 38.57 (t), 35.62 (t), 35.47 (d), 28.76 (t), 27.37 (t), 25.93 (q, SiCMe$_3$), 25.84 (q, SiCMe$_3$), 25.78 (q, SiCMe$_3$), 23.87 (q, C-27), 23.43 (t), 22.42 (t), 22.11 (t), 18.56 (q, C-21), 18.25 (s, SiCMe$_3$), 18.17 (s, 2×SiCMe$_3$), 12.30 (q, C-18), −4.38 (q, SiMe), −4.67 (q, SiMe), −4.87 (q, 3×SiMe), −5.09 (q, SiMe); exact mass calculated for C$_{44}$H$_{84}$O$_3$Si$_3$Na (MNa$^+$) 767.5626, found 767.5612.

The protected vitamin 16 (33 mg, 44 μmol) was dissolved in THF (2 mL) and acetonitrile (2 mL). A solution of aq. 48% HF in acetonitrile (1:9 ratio, 2 mL) was added at 0° C. and the resulting mixture was stirred at room temperature for 6 h. Saturated aq. NaHCO$_3$ solution was added and the reaction mixture was extracted with ethyl acetate. The combined organic phases were washed with brine, dried (Na$_2$SO$_4$) and concentrated under reduced pressure. The residue was diluted with 2 mL of hexane/ethyl acetate (8:2) and applied on a Waters silica Sep-Pak cartridge (2 g). An elution with hexane/ethyl acetate (8:2) and later with ethyl acetate gave the crude product 17 (18 mg). The vitamin 17 was further purified by reverse phase HPLC [9.4×250 mm Zorbax Eclipse XDB-C18 column, 3 mL/min, methanol/water (85:15) solvent system, R$_t$=10.81 min.] to give a colorless oil (13.97 mg, 79% yield):

UV (in EtOH) λ$_{max}$261.4, 252.4, 244.4 nm; $^1$H NMR (500 MHz, CDCl$_3$) δ 6.35 and 5.88 (1H and 1H, each d, J=11.2 Hz, 6- and 7-H), 5.10 and 5.08 (each 1H, each s, =CH$_2$), 4.47 (2H, m, 1β- and 3α-H), 3.78 (1H, m, 25-H), 2.84 (1H, dd, J=13.1, 4.4 Hz, 10β-H), 2.81 (1H, br d, J=11.9 Hz, 9β-H), 2.56 (1H, dd, J=13.4, 3.6 Hz, 4α-H), 2.32 (1H, dd, J=13.4, 6.1 Hz, 4β-H), 2.28 (1H, dd, J=13.1, 8.4 Hz, 10α-H), 1.18 (3H, d, J=6.2 Hz, 27-H$_3$), 0.84 (3H, d, J=6.5 Hz, 21-H$_3$), 0.543 (3H, s, 18-H$_3$); $^{13}$C NMR (125 MHz) δ 151.98 (s, C-2), 143.33 (s, C-8), 130.45 (s, C-5), 124.21 (d, C-6), 115.32 (d, C-7), 107.70 (t, =CH$_2$), 71.79 and 70.65 (each d, C-1 and C-3), 68.21 (d, C-25), 56.33 (d), 56.14 (d), 45.80 (t), 45.80 (s, C-13), 40.34 (t), 39.69 (t), 38.14 (t), 35.50 (t), 35.39 (d), 28.94 (t), 27.27 (t), 23.53 (q, C-27), 23.48 (t), 22.41 (t), 22.14 (t), 18.52 (q, C-21), 12.34 (q, C-18); MS (EI) m/z 402 (100, M$^+$), 384 (9, M$^+$-H$_2$O), 369 (9, M$^+$-H$_2$O—CH$_3$), 351 (6, M$^+$-2H$_2$O—CH$_3$), 317 (31), 287 (38, M$^+$-C$_7$H$_{15}$O), 269 (39), 251 (36), 192 (19), 161 (40), 147 (65), 135 (85); exact mass calculated for C$_{26}$H$_{42}$O$_3$ (M$^+$) 402.3134, found 402.3127.

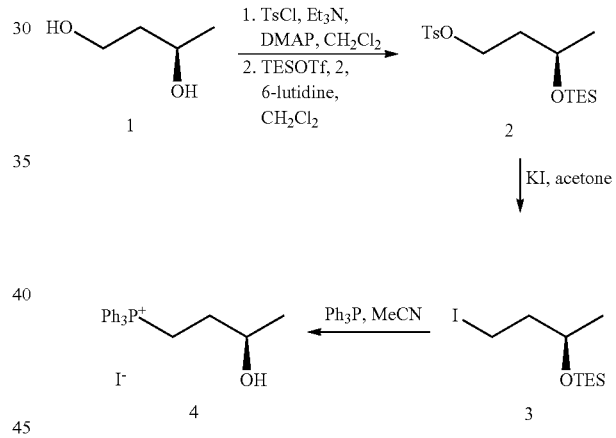

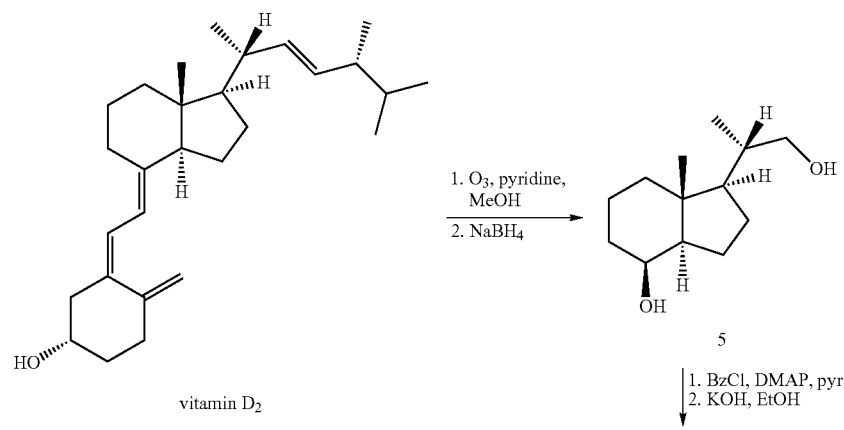

Scheme 2

-continued
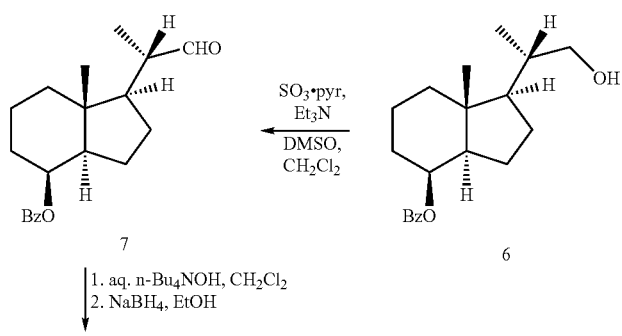
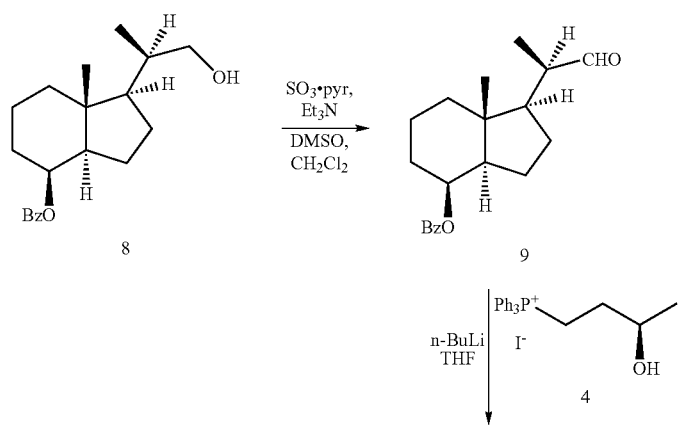
Scheme 3
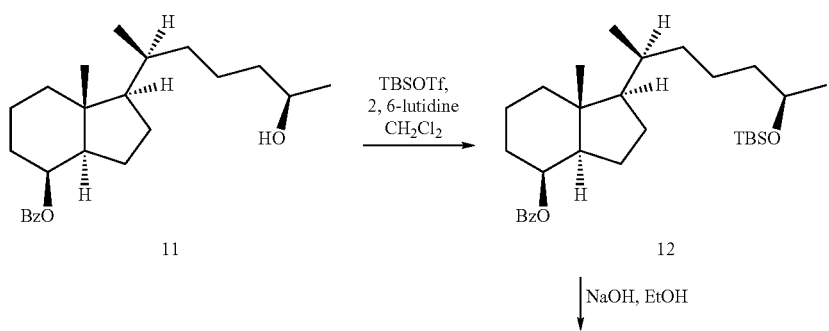

-continued

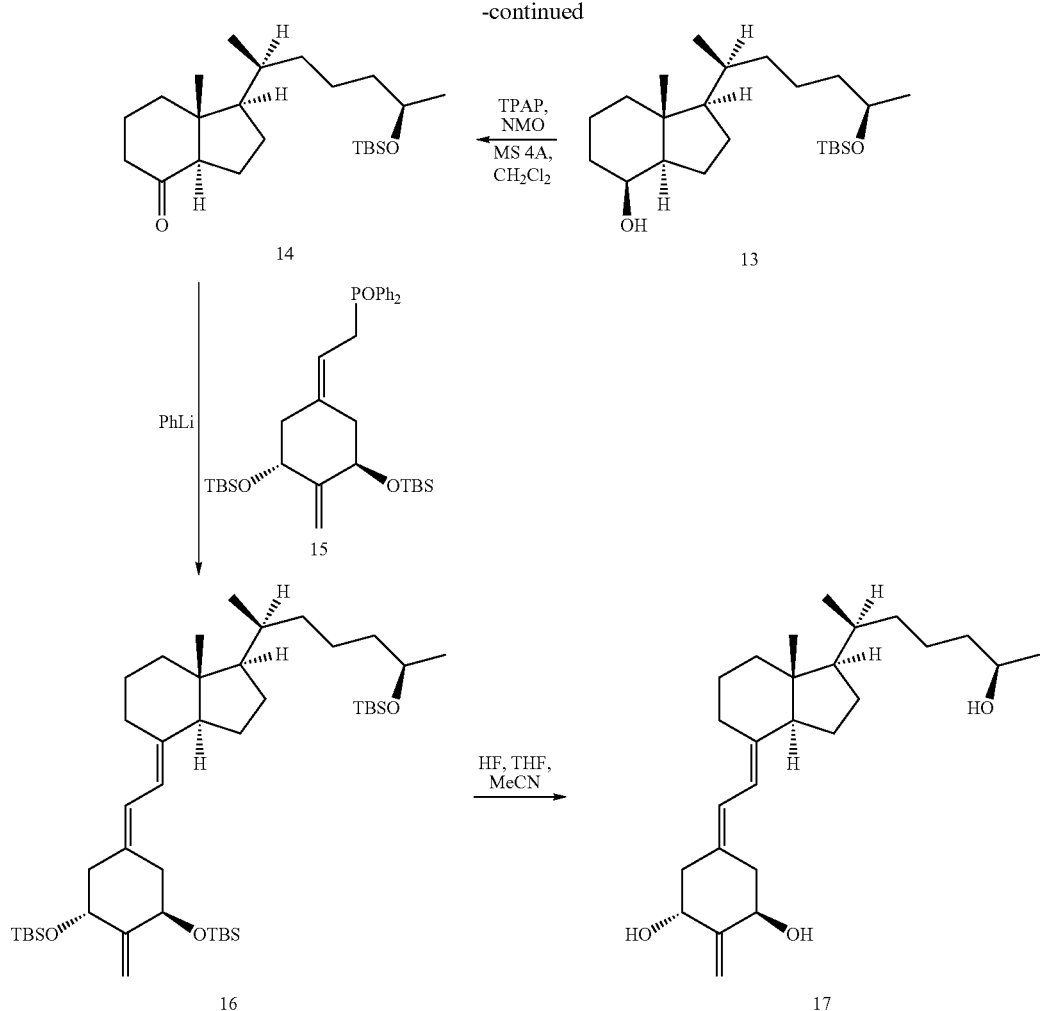

Biological Activity of 2-methylene-(20S,25R)-19,26-dinor-1α,25-dihydroxyvitamin $D_3$ The introduction of a methylene group to the 2-position, a methyl group at the 20-position (C-20) in its S-configuration, the replacement of the methyl group typically located at the 26 position (C-26) in the side chain with a hydrogen atom, and the hydroxyl group at the 25-position (C-25) in its R-configuration, had little effect on binding of SR1 to the full length recombinant rat vitamin D receptor, as compared to 1α,25-dihydroxyvitamin $D_3$. The compound SR1 bound with nearly the same affinity to the nuclear vitamin D receptor as compared to the standard 1,25-$(OH)_2D_3$ (FIG. 1). It might be expected from these results that compound SR1 would have equivalent biological activity. Surprisingly, however, compound SR1 is a highly selective analog with unique biological activity.

Figure 5A:
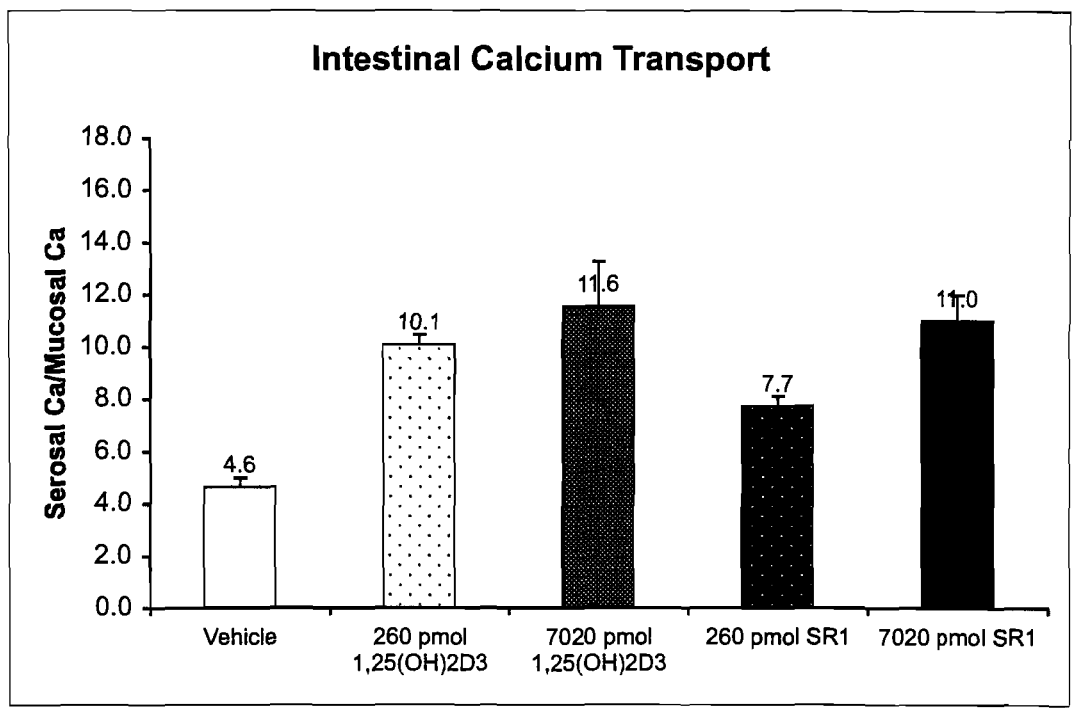
FIG. 5A is a bar graph illustrating the intestinal calcium transport activity of 1,25$(OH)_2D_3$ as compared to SR1 in a first experiment using a first group of animals.
Figure 5B:
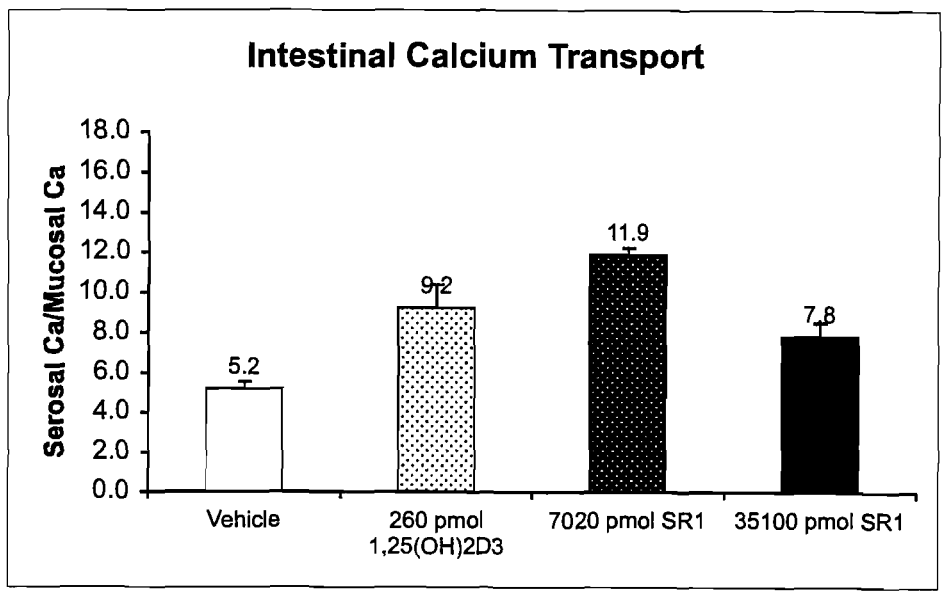
FIG. 5B is a bar graph illustrating the intestinal calcium transport activity of 1,25$(OH)_2D_3$ as compared to SR1 in a second experiment using a second group of animals.

FIGS. 5A and 5B show that SR1 has some ability to increase intestinal calcium transport activity in vivo, in a dose dependent manner, but it clearly has very little activity as compared to that of 1,25-dihydroxyvitamin $D_3$ (1,25$(OH)_2D_3$), the natural hormone, in stimulating intestinal calcium transport. In two batches of rats, SR1 failed to stimulate intestinal calcium transport as potently as 1,25$(OH)_2D_3$.

Figure 4A:
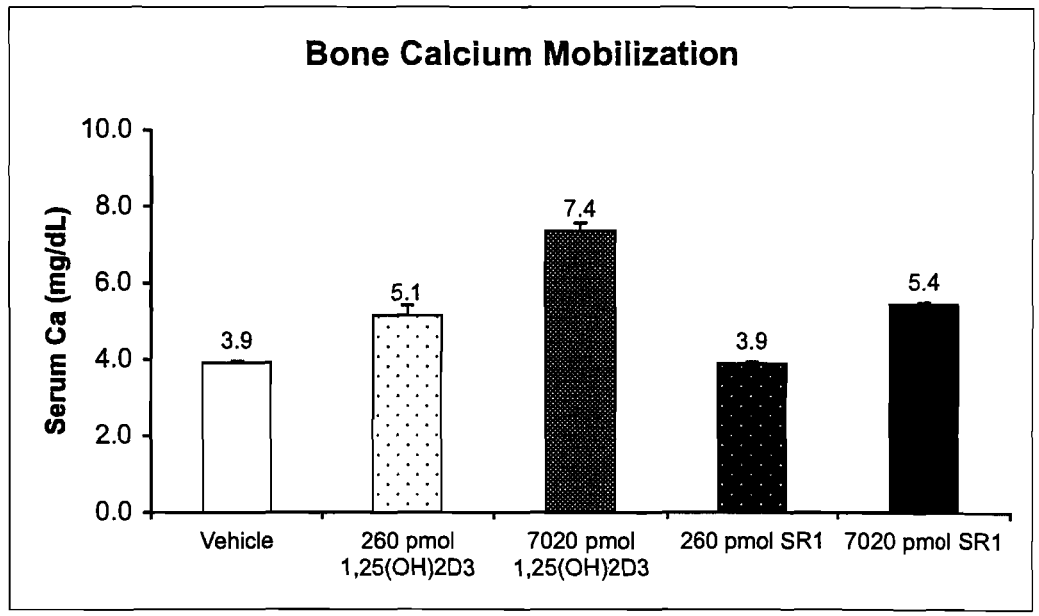
FIG. 4A is a bar graph illustrating the bone calcium mobilization activity of 1,25$(OH)_2D_3$ as compared to SR1 in a first experiment using a first group of animals.
Figure 4B:
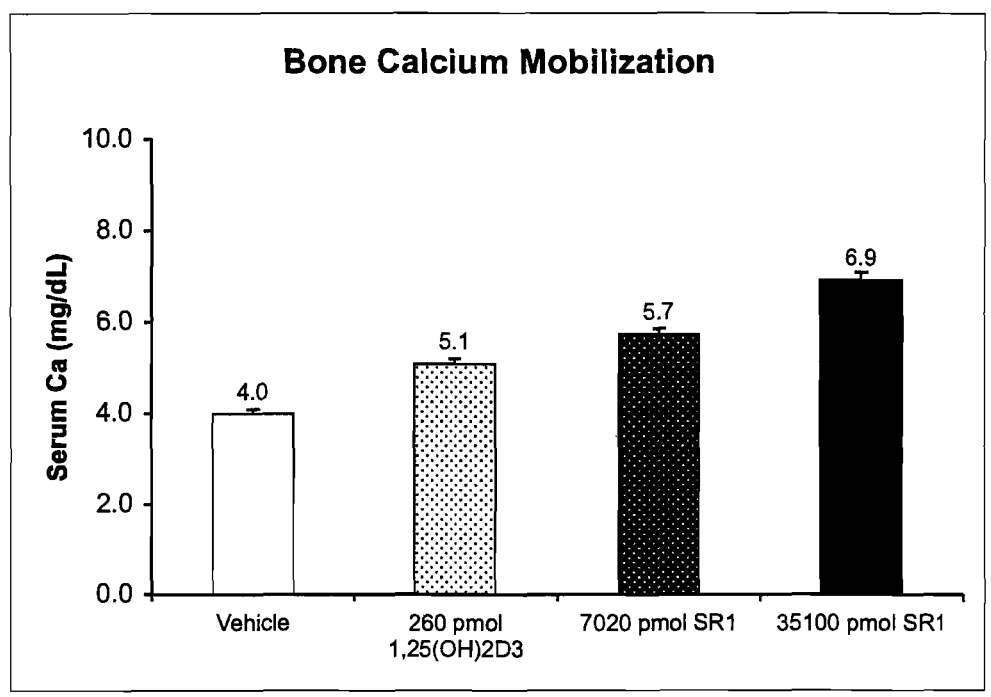
FIG. 4B is a bar graph illustrating the bone calcium mobilization activity of 1,25$(OH)_2D_3$ as compared to SR1 in a second experiment using a second group of animals.

FIGS. 4A and 4B demonstrate that SR1 has very little bone calcium mobilization activity, as compared to 1,25$(OH)_2D_3$.

Two separate studies clearly show that SR1 has significantly less bone calcium mobilization activity compared to 1,25$(OH)_2D_3$. SR1 is approximately 30 times less potent than the native hormone in mobilizing bone calcium store.

FIGS. 4 and 5 thus illustrate that SR1 may be characterized as having little, if any, calcemic activity.

Figure 2:
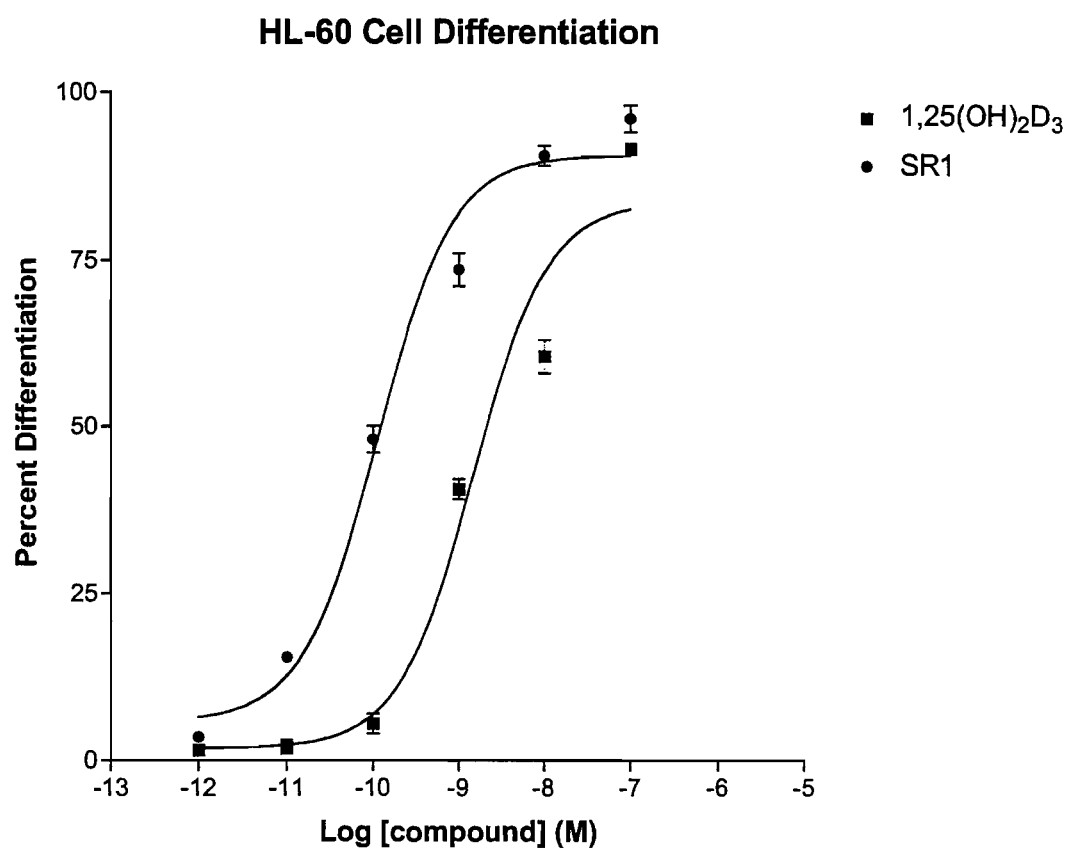

FIG. 2 illustrates that SR1 is about 10 times more potent than 1,25$(OH)_2D_3$ on HL-60 cell differentiation, i.e. causing the differentiation of HL-60 cells into monocytes, making it an excellent candidate for the treatment of psoriasis and cancer, especially against leukemia, colon cancer, breast cancer, skin cancer and prostate cancer. In addition, due to its relatively high cell differentiation activity, this compound provides a therapeutic agent for the treatment of various skin conditions including wrinkles, lack of adequate dermal hydration, i.e. dry skin, lack of adequate skin firmness, i.e. slack skin, and insufficient sebum secretion. Use of this compound thus not only results in moisturizing of skin but also improves the barrier function of skin.

Figure 3:
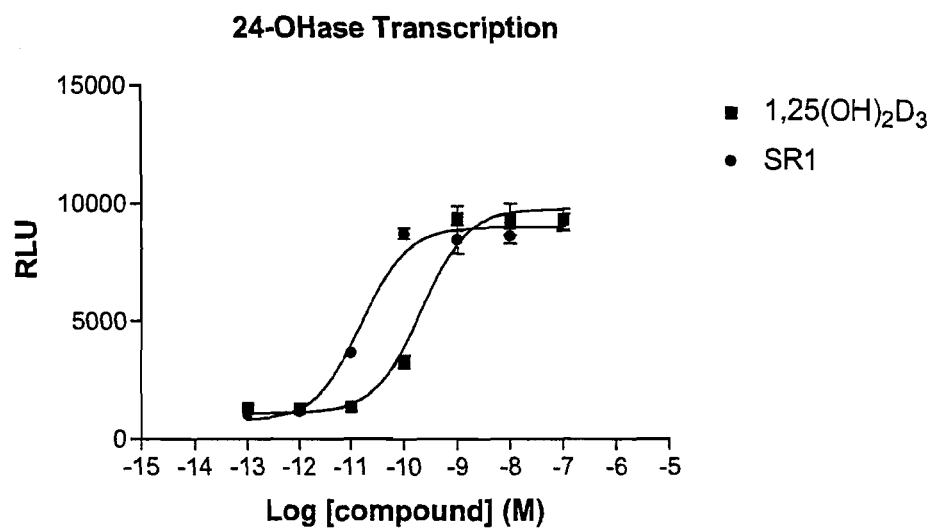

FIG. 3 illustrates that in bone cells the compound SR1 is one log more potent than 1,25$(OH)_2D_3$ in increasing transcription of the 24-hydroxylase gene. This result, together with the cell differentiation activity of FIG. 2, suggests that SR1 will be very effective in psoriasis because it has direct cellular activity in causing cell differentiation, gene transcription, and in suppressing cell growth. These data also indicate that SR1 may have significant activity as an anti-cancer agent, especially against leukemia, colon cancer, breast cancer, skin cancer and prostate cancer.

The strong activity of SR1 on HL-60 differentiation suggests it will be active in suppressing growth of parathyroid glands and in the suppression of the preproparathyroid gene.

Experimental Methods

Vitamin D Receptor Binding
Test Material
Protein Source

Full-length recombinant rat receptor was expressed in *E. coli* BL21 (DE3) Codon Plus RIL cells and purified to homogeneity using two different column chromatography systems. The first system was a nickel affinity resin that utilizes the C-terminal histidine tag on this protein. The protein that was eluted from this resin was further purified using ion exchange chromatography (S-Sepharose Fast Flow). Aliquots of the purified protein were quick frozen in liquid nitrogen and stored at −80° C. until use. For use in binding assays, the protein was diluted in TEDK$_{50}$ (50 mM Tris, 1.5 mM EDTA, pH7.4, 5 mM DTT, 150 mM KCl) with 0.1% Chaps detergent. The receptor protein and ligand concentration were optimized such that no more than 20% of the added radiolabeled ligand was bound to the receptor.

Study Drugs

Unlabeled ligands were dissolved in ethanol and the concentrations determined using UV spectrophotometry (1,25 (OH)$_2$D$_3$: molar extinction coefficient=18,200 and $\lambda_{max}$=265 nm; Analogs: molar extinction coefficient=42,000 and $\lambda_{max}$=252 nm). Radiolabeled ligand ($^3$H-1,25(OH)$_2$D$_3$, ~159 Ci/mmole) was added in ethanol at a final concentration of 1 nM.

Assay Conditions

Radiolabeled and unlabeled ligands were added to 100 mcl of the diluted protein at a final ethanol concentration of ≤10%, mixed and incubated overnight on ice to reach binding equilibrium. The following day, 100 mcl of hydroxylapatite slurry (50%) was added to each tube and mixed at 10-minute intervals for 30 minutes. The hydroxylapaptite was collected by centrifugation and then washed three times with Tris-EDTA buffer (50 mM Tris, 1.5 mM EDTA, pH 7.4) containing 0.5% Titron X-100. After the final wash, the pellets were transferred to scintillation vials containing 4 ml of Biosafe II scintillation cocktail, mixed and placed in a scintillation counter. Total binding was determined from the tubes containing only radiolabeled ligand.

HL-60 Differentiation
Test Material
Study Drugs

The study drugs were dissolved in ethanol and the concentrations determined using UV spectrophotometry. Serial dilutions were prepared so that a range of drug concentrations could be tested without changing the final concentration of ethanol (≤0.2%) present in the cell cultures.

Cells

Human promyelocytic leukemia (HL60) cells were grown in RPMI-1640 medium containing 10% fetal bovine serum. The cells were incubated at 37° C. in the presence of 5% CO$_2$.

Assay Conditions

HL60 cells were plated at 1.2×10$^5$ cells/ml. Eighteen hours after plating, cells in duplicate were treated with drug. Four days later, the cells were harvested and a nitro blue tetrazolium reduction assay was performed (Collins et al., 1979; J. Exp. Med. 149:969-974). The percentage of differentiated cells was determined by counting a total of 200 cells and recording the number that contained intracellular black-blue formazan deposits. Verification of differentiation to monocytic cells was determined by measuring phagocytic activity (data not shown).

In Vitro Transcription Assay

Transcription activity was measured in ROS 17/2.8 (bone) cells that were stably transfected with a 24-hydroxylase (24Ohase) gene promoter upstream of a luciferase reporter gene (Arbour et al., 1998). Cells were given a range of doses. Sixteen hours after dosing the cells were harvested and luciferase activities were measured using a luminometer.

RLU=relative luciferase units.

Intestinal Calcium Transport and Bone Calcium Mobilization

Male, weanling Sprague-Dawley rats were placed on Diet 11 (0.47% Ca) diet+AEK oil for one week followed by Diet 11 (0.02% Ca)+AEK oil for 3 weeks. The rats were then switched to a diet containing 0.47% Ca for one week followed by two weeks on a diet containing 0.02% Ca. Dose administration began during the last week on 0.02% calcium diet. Four consecutive ip doses were given approximately 24 hours apart. Twenty-four hours after the last dose, blood was collected from the severed neck and the concentration of serum calcium determined as a measure of bone calcium mobilization. The first 10 cm of the intestine was also collected for intestinal calcium transport analysis using the everted gut sac method.

Interpretation of Data

Summary of Biological Findings.

This compound binds the VDR with nearly the same affinity as the native hormone, but displays approximately 10 times greater cell differentiation activity and in vitro gene transcription activity compared to 1,25(OH)$_2$D$_3$. In vivo this compound exhibits significantly less bone calcium mobilization and intestinal calcium transport activities compared to the native hormone making this compound a potentially valuable agent for the treatment of such diseases as cancer, secondary hyperparathyroidism, renal osteodystrophy, autoimmune diseases, skin conditions, and psoriasis.

VDR Binding, HL60 Cell Differentiation, and Transcription Activity.

SR1 ($K_i$=8×10$^{-11}$M) is nearly as active as the natural hormone 1α,25-dihydroxyvitamin D$_3$ ($K_i$=1×10$^{-10}$M) in its ability to compete with [$^3$H]-1,25(OH)$_2$D$_3$ for binding to the full-length recombinant rat vitamin D receptor (FIG. 1). SR1 displays about 10 times greater activity (EC$_{50}$=1×10$^{-10}$M) in its ability (efficacy or potency) to promote HL-60 cell differentiation as compared to 1α,25-dihydroxyvitamin D$_3$ (EC$_{50}$=2×10$^{-9}$M) (See FIG. 2). Also, compound SR1 (EC$_{50}$=1×10$^{-11}$M) has 10 times greater transcriptional activity in bone cells than 1α,25-dihydroxyvitamin D$_3$ (EC$_{50}$=2×10$^{-10}$M) (See FIG. 3). These results suggest that SR1 will be very effective in psoriasis because it has direct cellular activity in causing cell differentiation, gene transcription, and in suppressing cell growth. These data also indicate that SR1 will have significant activity as an anti-cancer agent, especially against leukemia, colon cancer, breast cancer, skin cancer and prostate cancer, as well as against skin conditions such as dry skin (lack of dermal hydration), undue skin slackness (insufficient skin firmness), insufficient sebum secretion and wrinkles. It would also be expected to be very active in suppressing secondary hyperparathyroidism, especially in subjects having chronic kidney disease and subjects on dialysis.

Calcium Mobilization from Bone and Intestinal Calcium Absorption in Vitamin D-Deficient Animals.

Using vitamin D-deficient rats on a low calcium diet (0.02%), the activities of SR1 and $1,25(OH)_2D_3$ in intestine and bone were tested. As expected, the native hormone $(1,25(OH)_2D_3)$ increased serum calcium levels at all dosages (FIGS. 4A and 4B). The two separate studies reported in FIGS. 4A and 4B show that SR1 has little, if any, activity in mobilizing calcium from bone. Administration of SR1 at 260 pmol/day for 4 consecutive days did not result in mobilization of bone calcium, and increasing the amount of SR1 to 7020 pmol/day was also without any substantial effect.

Intestinal calcium transport was evaluated in the same groups of animals using the everted gut sac method (FIGS. 5A and 5B). These results show that the compound SR1 promotes intestinal calcium transport only slightly when administered at 260 pmol/day, whereas $1,25(OH)_2D_3$ promotes a significant increase at the 260 pmol/day dose. It was only when 7020 pmol/day of SR1 was administered that significant intestinal calcium transport activity was recorded, an almost 30-fold increase in dosage over the 260 pmol/day dose. Thus, it may be concluded that SR1 is essentially devoid of intestinal calcium transport activity at the recommended lower doses.

These results illustrate that SR1 is an excellent candidate for numerous human therapies as described herein, and that it may be particularly useful in a number of circumstances such as suppression of secondary hyperparathyroidism of renal osteodystrophy, autoimmune diseases, cancer, numerous types of skin conditions, and psoriasis. SR1 is an excellent candidate for treating psoriasis because: (1) it has significant VDR binding, transcription activity and cellular differentiation activity; (2) it is devoid of hypercalcemic liability at relatively low doses, unlike $1,25(OH)_2D_3$; and (3) it is easily synthesized. Since SR1 has significant binding activity to the vitamin D receptor, but has little ability to raise blood serum calcium, it may also be particularly useful for the treatment of secondary hyperparathyroidism, especially in subjects diagnosed with chronic kidney disease and subjects on dialysis, as well as the treatment of renal osteodystrophy.

These data also indicate that the compound SR1 of the invention may be especially suited for treatment and prophylaxis of human disorders which are characterized by an imbalance in the immune system, e.g. in autoimmune diseases, including multiple sclerosis, lupus, diabetes mellitus, host versus graft rejection, and rejection of organ transplants; and additionally for the treatment of inflammatory diseases, such as rheumatoid arthritis, asthma, and inflammatory bowel diseases such as celiac disease, ulcerative colitis and Crohn's disease. Acne, alopecia and hypertension are other conditions which may be treated with the compound SR1 of the invention.

The compounds of the invention of formula I, and particularly formula Ia, are also useful in preventing or treating obesity, inhibiting adipocyte differentiation, inhibiting SCD-1 gene transcription, and/or reducing body fat in animal subjects. Therefore, in some embodiments, a method of preventing or treating obesity, inhibiting adipocyte differentiation, inhibiting SCD-1 gene transcription, and/or reducing body fat in an animal subject includes administering to the animal subject, an effective amount of one or more of the compounds or a pharmaceutical composition that includes one or more of the compounds of formula I. Administration of the compound or the pharmaceutical compositions to the subject inhibits adipocyte differentiation, inhibits gene transcription, and/or reduces body fat in the animal subject. The animal may be a human, a domestic animal such as a dog or a cat, or an agricultural animal, especially those that provide meat for human consumption, such as fowl like chickens, turkeys, pheasant or quail, as well as bovine, ovine, caprine, or porcine animals.

For prevention and/or treatment purposes, the compounds of this invention defined by formula I may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compounds of formula I and particularly SR1, may be administered orally, topically, parenterally, rectally, nasally, sublingually or transdermally. The compound is advantageously administered by injection or by intravenous infusion or suitable sterile solutions, or in the form of liquid or solid doses via the alimentary canal, or in the form of creams, ointments, patches, or similar vehicles suitable for transdermal applications. A dose of from 0.01 µg to 1000 µg per day of the compounds I, particularly SR1, preferably from about 0.1 µg to about 500 µg per day, is appropriate for prevention and/or treatment purposes, such dose being adjusted according to the disease to be treated, its severity and the response of the subject as is well understood in the art. Since the compound exhibits specificity of action, each may be suitably administered alone, or together with graded doses of another active vitamin D compound—e.g. 1α-hydroxyvitamin $D_2$ or $D_3$, or 1α,25-dihydroxyvitamin $D_3$—in situations where different degrees of bone mineral mobilization and calcium transport stimulation is found to be advantageous.

Compositions for use in the above-mentioned treatments comprise an effective amount of the compounds I, particularly SR1, as defined by the above formula I and Ia as the active ingredient, and a suitable carrier. An effective amount of such compound for use in accordance with this invention is from about 0.01 µg to about 1000 µg per gm of composition, preferably from about 0.1 µg to about 500 µg per gram of composition, and may be administered topically, transdermally, orally, rectally, nasally, sublingually, or parenterally in dosages of from about 0.01 µg/day to about 1000 µg/day, and preferably from about 0.1 µg/day to about 500 µg/day.

The compounds I, particularly SR1, may be formulated as creams, lotions, ointments, topical patches, pills, capsules or tablets, suppositories, aerosols, or in liquid form as solutions, emulsions, dispersions, or suspensions in pharmaceutically innocuous and acceptable solvent or oils, and such preparations may contain in addition other pharmaceutically innocuous or beneficial components, such as stabilizers, antioxidants, emulsifiers, coloring agents, binders or taste-modifying agents.

The compounds I, particularly SR1, may be advantageously administered in amounts sufficient to effect the differentiation of promyelocytes to normal macrophages. Dosages as described above are suitable, it being understood that the amounts given are to be adjusted in accordance with the severity of the disease, and the condition and response of the subject as is well understood in the art.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For nasal administration, inhalation of powder, self-propelling or spray formulations, dispensed with a spray can, a nebulizer or an atomizer can be used. The formulations, when dispensed, preferably have a particle size in the range of 10 to 100μ.

The formulations may conveniently be presented in dosage unit form and may be prepared by any of the methods well known in the art of pharmacy. By the term "dosage unit" is meant a unitary, i.e. a single dose which is capable of being administered to a patient as a physically and chemically stable unit dose comprising either the active ingredient as such or a mixture of it with solid or liquid pharmaceutical diluents or carriers.

We claim:

1. A compound having the formula:

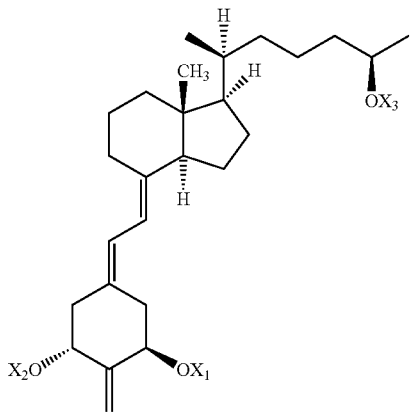

I where $X_1$, $X_2$ and $X_3$, which may be the same or different, are each selected from hydrogen or a hydroxy-protecting group.

2. The compound of claim 1 wherein $X_3$ is hydrogen.
3. The compound of claim 1 wherein $X_1$ is hydrogen.
4. The compound of claim 1 wherein $X_1$, $X_2$ and $X_3$ are all t-butyldimethylsilyl.
5. A pharmaceutical composition containing an effective amount of at least one compound as claimed in claim 1 together with a pharmaceutically acceptable excipient.
6. The pharmaceutical composition of claim 5 wherein said effective amount comprises from about 0.01 μg to about 1000 μg per gram of composition.
7. The pharmaceutical composition of claim 5 wherein said effective amount comprises from about 0.1 μg to about 500 μg per gram of composition.

8. 2-methylene-(20S,25R)-19,26-dinor-1α,25-dihydroxyvitamin $D_3$ having the formula:

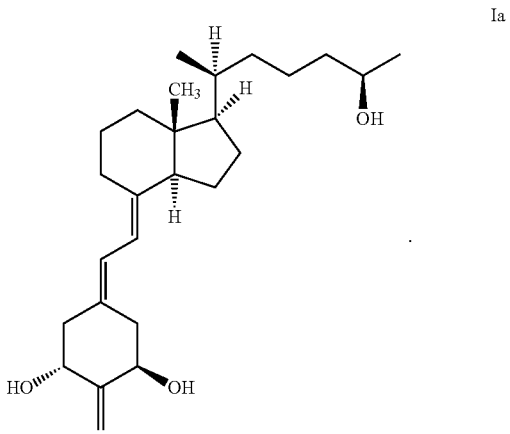

Ia

9. A pharmaceutical composition containing an effective amount of 2-methylene-(20S,25R)-19,26-dinor-1α,25-dihydroxyvitamin $D_3$ together with a pharmaceutically acceptable excipient.
10. The pharmaceutical composition of claim 9 wherein said effective amount comprises from about 0.01 μg to about 1000 μg per gram of composition.
11. The pharmaceutical composition of claim 9 wherein said effective amount comprises from about 0.1 μg to about 500 μg per gram of composition.
12. A method of treating psoriasis comprising administering to a subject with psoriasis an effective amount of a compound having the formula:

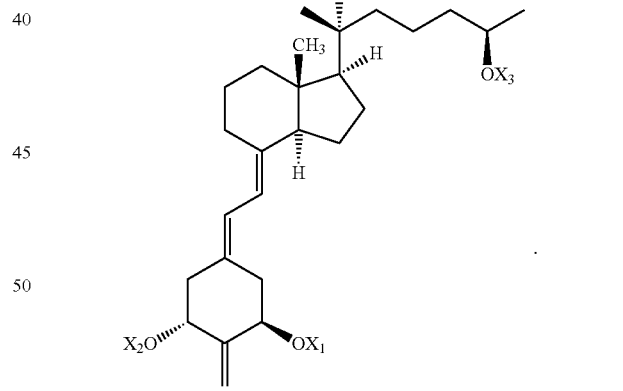

I where $X_1$, $X_2$ and $X_3$ which may be the same or different, are each selected from hydrogen or a hydroxy-protecting group.

13. The method of claim 12 wherein the compound is administered orally.
14. The method of claim 12 wherein the compound is administered parenterally.
15. The method of claim 12 wherein the compound is administered transdermally.
16. The method of claim 12 wherein the compound is administered topically.
17. The method of claim 12 wherein the compound is administered rectally.

18. The method of claim 12 wherein the compound is administered nasally.

19. The method of claim 12 wherein the compound is administered sublingually.

20. The method of claim 12 wherein the compound is administered in a dosage of from about 0.01 µg/day to about 1000 µg/day.

21. The method of claim 12 wherein the compound is 2-methylene-(20S,25R)-19,26-dinor-1α,25-dihydroxyvitamin D₃ having the formula:

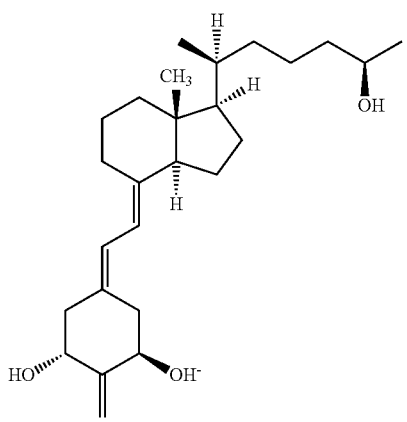

Ia

22. A method of treating a disease selected from the group consisting of leukemia, colon cancer, breast cancer, skin cancer or prostate cancer comprising administering to a subject with said disease an effective amount of a compound having the formula:

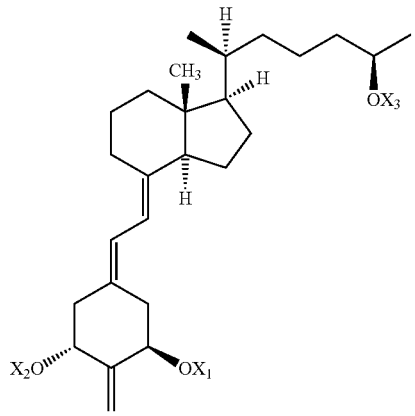

I where $X_1$, $X_2$ and $X_3$ which may be the same or different, are each selected from hydrogen or a hydroxy-protecting group.

23. The method of claim 22 wherein the compound is administered orally.

24. The method of claim 22 wherein the compound is administered parenterally.

25. The method of claim 22 wherein the compound is administered transdermally.

26. The method of claim 22 wherein the compound is administered rectally.

27. The method of claim 22 wherein the compound is administered nasally.

28. The method of claim 22 wherein the compound is administered sublingually.

29. The method of claim 22 wherein the compound is administered in a dosage of from about 0.01 µg/day to about 1000 µg/day.

30. The method of claim 22 wherein the compound is 2-methylene-(20S,25R)-19,26-dinor-1α,25-dihydroxyvitamin D₃ having the formula:

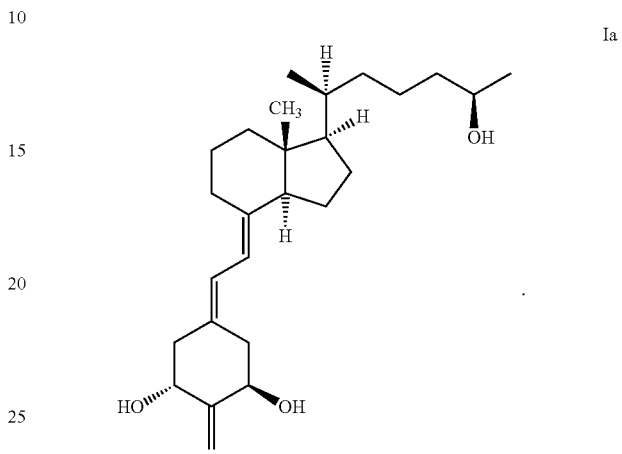

Ia

31. A method of treating an autoimmune disease selected from the group consisting of multiple sclerosis, lupus, diabetes mellitus, host versus graft rejection, and rejection of organ transplants, comprising administering to a subject with said disease an effective amount of a compound having the formula:

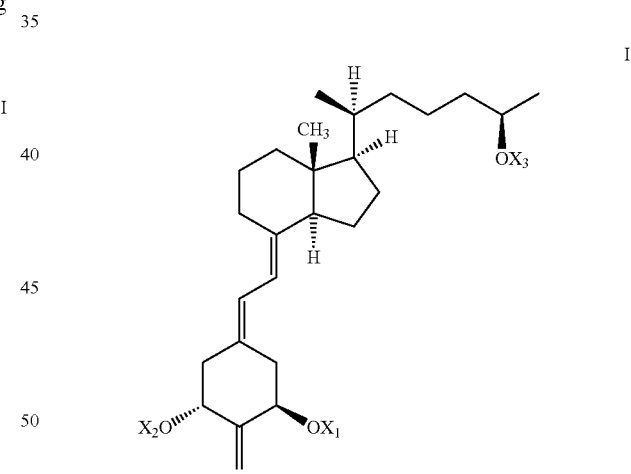

I where $X_1$, $X_2$ and $X_3$ which may be the same or different, are each selected from hydrogen or hydroxy-protecting group.

32. The method of claim 31 wherein the compound is administered orally.

33. The method of claim 31 wherein the compound is administered parenterally.

34. The method of claim 31 wherein the compound is administered transdermally.

35. The method of claim 31 wherein the compound is administered rectally.

36. The method of claim 31 wherein the compound is administered nasally.

37. The method of claim 31 wherein the compound is administered sublingually.

38. The method of claim 31 wherein the compound is administered in a dosage of from about 0.01 μg/day to about 1000 μg/day.

39. The method of claim 31 wherein the compound is 2-methylene-(20S,25R)-19,26-dinor-1α,25-dihydroxyvitamin D₃ having the formula:

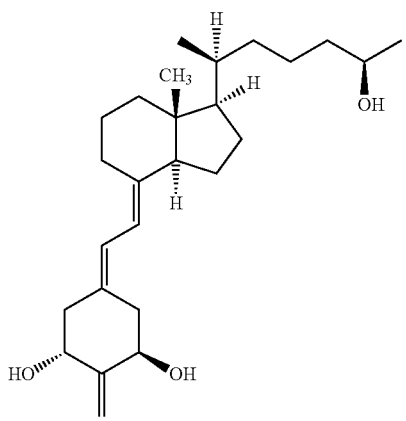

Ia

40. A method of treating an inflammatory disease selected from the group consisting of rheumatoid arthritis, asthma, and inflammatory bowel diseases, comprising administering to a subject with said disease an effective amount of a compound having the formula:

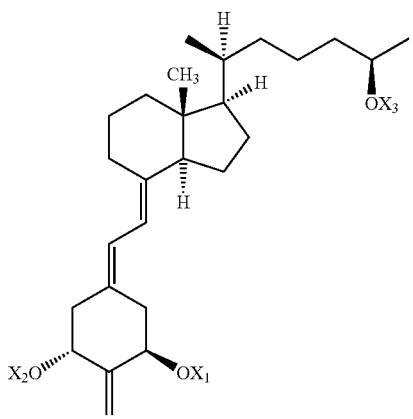

I where $X_1$, $X_2$ and $X_3$, which may be the same or different, are each selected from hydrogen or a hydroxy-protecting group.

41. The method of claim 40 wherein the compound is administered orally.

42. The method of claim 40 wherein the compound is administered parenterally.

43. The method of claim 40 wherein the compound is administered transdermally.

44. The method of claim 40 wherein the compound is administered rectally.

45. The method of claim 40 wherein the compound is administered nasally.

46. The method of claim 40 wherein the compound is administered sublingually.

47. The method of claim 40 wherein the compound is administered in a dosage of from about 0.01 μg/day to about 1000 μg/day.

48. The method of claim 40 wherein the compound is 2-methylene-(20S,25R)-19,26-dinor-1α,25-dihydroxyvitamin D₃ having the formula:

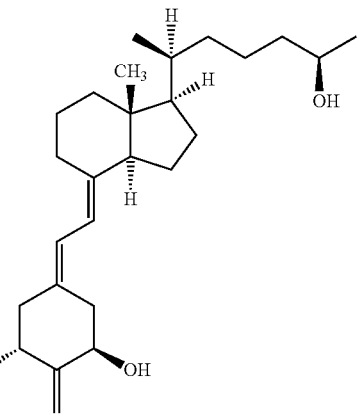

Ia

49. A method of treating a skin condition selected from the group consisting of wrinkles, lack of adequate skin firmness, lack of adequate dermal hydration and insufficient sebum secretion which comprises administering to a subject with said skin condition an effective amount of a compound having the formula:

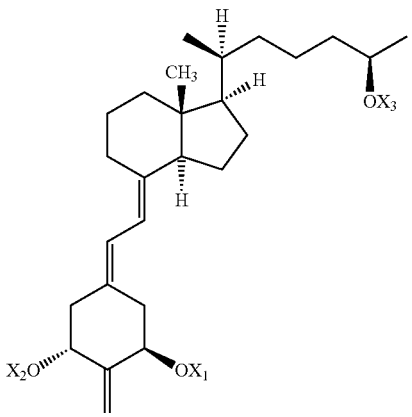

I where $X_1$, $X_2$ and $X_3$ which may be the same or different, are each selected from hydrogen or a hydroxy-protecting group.

50. The method of claim 49 wherein the compound is administered orally.

51. The method of claim 49 wherein the compound is administered parenterally.

52. The method of claim 49 wherein the compound is administered transdermally.

53. The method of claim 49 wherein the compound is administered topically.

54. The method of claim 49 wherein the compound is administered rectally.

55. The method of claim 49 wherein the compound is administered nasally.

56. The method of claim 49 wherein the compound is administered sublingually.

57. The method of claim 49 wherein the compound is administered in a dosage of from about 0.01 μg/day to about 1000 μg/day.

58. The method of claim 49 wherein the compound is 2-methylene-(20S,25R)-19,26-dinor-1α,25-dihydroxyvitamin D₃ having the formula:

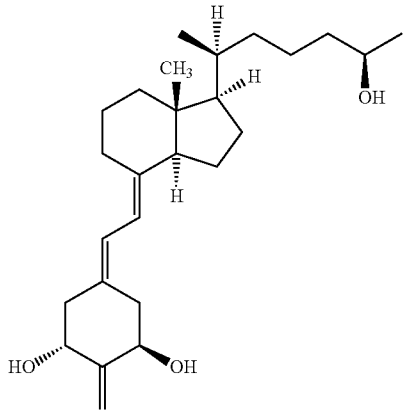

59. A method of treating renal osteodystrophy comprising administering to a subject with renal osteodystrophy an effective amount of a compound having the formula:

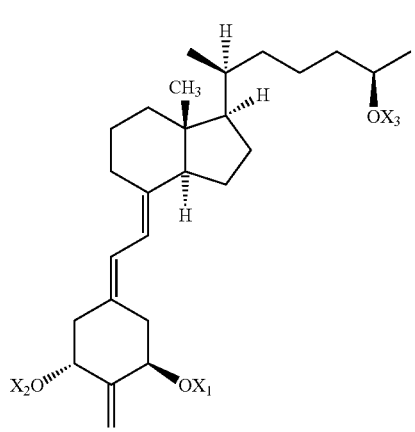

where $X_1$, $X_2$ and $X_3$, which may be the same or different, are each selected from hydrogen or a hydroxy-protecting group.

60. The method of claim 59 wherein the compound is administered orally.

61. The method of claim 59 wherein the compound is administered parenterally.

62. The method of claim 59 wherein the compound is administered transdermally.

63. The method of claim 59 wherein the compound is administered rectally.

64. The method of claim 59 wherein the compound is administered nasally.

65. The method of claim 59 wherein the compound is administered sublingually.

66. The method of claim 59 wherein the compound is administered in a dosage of from about 0.01 µg/day to about 1000 µg/day.

67. The method of claim 59 wherein the compound is 2-methylene-(20S,25R)-19,26-dinor-1α,25-dihydroxyvitamin D₃ having the formula:

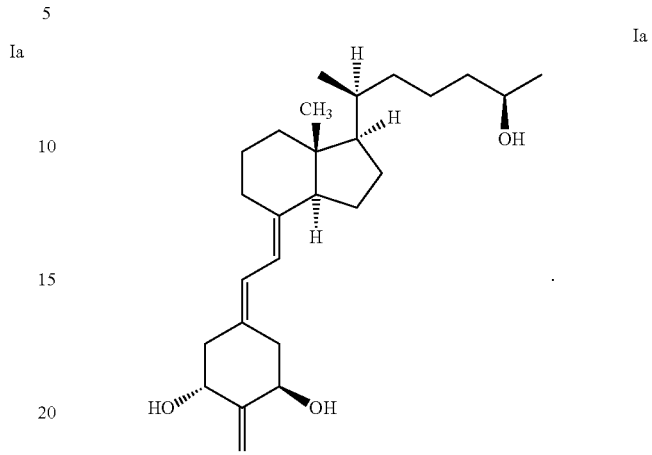

68. A method of treating obesity of an animal, inhibiting adipocyte differentiation, inhibiting SCD-1 gene transcription, and/or reducing body fat in an animal comprising administering to an animal in need thereof an effective amount of a compound having the formula:

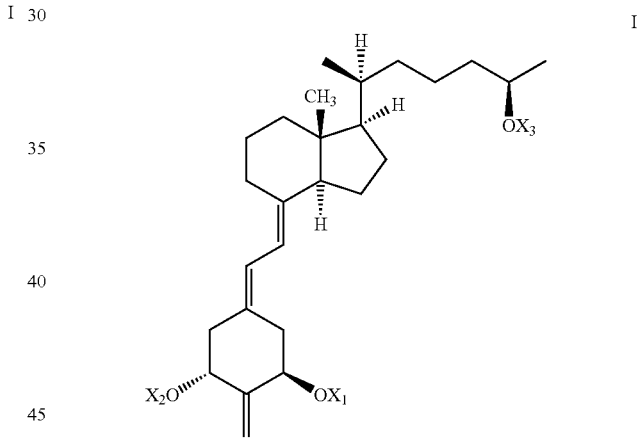

where $X_1$, $X_2$ and $X_3$, which may be the same or different, are each selected from hydrogen or a hydroxy-protecting group.

69. The method of claim 68 wherein the compound is administered orally.

70. The method of claim 68 wherein the compound is administered parenterally.

71. The method of claim 68 wherein the compound is administered transdermally.

72. The method of claim 68 wherein the compound is administered rectally.

73. The method of claim 68 wherein the compound is administered nasally.

74. The method of claim 68 wherein the compound is administered sublingually.

75. The method of claim 68 wherein the compound is administered in a dosage of from about 0.01 µg/day to about 1000 µg/day.

76. The method of claim 68 wherein the compound is 2-methylene-(20S,25R)-19,26-dinor-1α,25-dihydroxyvitamin D₃ having the formula:

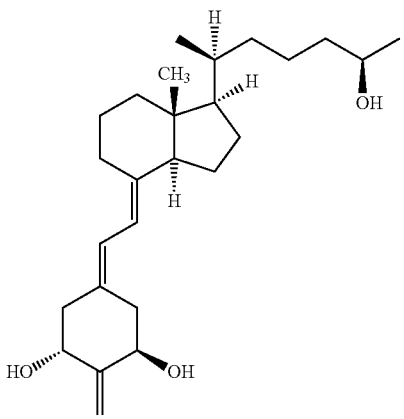

77. The method of claim 68 wherein the animal is a human.
78. The method of claim 68 wherein the animal is a domestic animal.
79. The method of claim 68 wherein the animal is an agricultural animal.
80. A method of treating secondary hyperparathyroidism comprising administering to a subject with secondary hyperparathyroidism an effective amount of a compound having the formula:

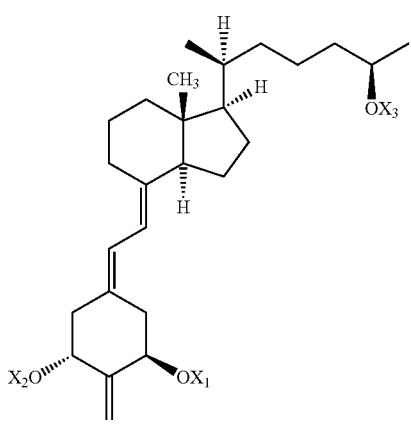

where $X_1$, $X_2$ and $X_3$, which may be the same or different, are each selected from hydrogen or a hydroxy-protecting group.

81. The method of claim 80 wherein the compound is administered orally.
82. The method of claim 80 wherein the compound is administered parenterally.
83. The method of claim 80 wherein the compound is administered transdermally.
84. The method of claim 80 wherein the compound is administered rectally.
85. The method of claim 80 wherein the compound is administered nasally.
86. The method of claim 80 wherein the compound is administered sublingually.
87. The method of claim 80 wherein the compound is administered in a dosage of from about 0.01 µg/day to about 1000 µg/day.
88. The method of claim 80 wherein the compound is 2-methylene-(20S,25R)-19,26-dinor-1α,25-dihydroxyvitamin $D_3$ having the formula:

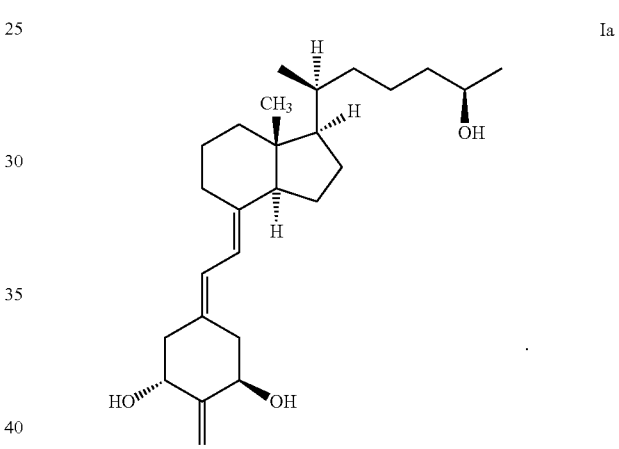

89. The method of claim 80 wherein the subject has chronic kidney disease.
90. The method of claim 80 wherein the subject is on dialysis.

* * * * *